US009687547B2

(12) United States Patent
Stenler et al.

(10) Patent No.: US 9,687,547 B2
(45) Date of Patent: Jun. 27, 2017

(54) T20 CONSTRUCTS FOR ANTI-HIV (HUMAN IMMUNODEFICIENCY VIRUS) THERAPY AND/OR VACCINES

(71) Applicant: Immunomedics, Inc., Morris Plains, NJ (US)

(72) Inventors: Sofia Stenler, Stockholm (SE); Britta Wahren, Stockholm (SE); Chien-Hsing Chang, Downingtown, PA (US); David M. Goldenberg, Mendham, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 0 days.

(21) Appl. No.: 15/164,437

(22) Filed: May 25, 2016

(65) Prior Publication Data
US 2016/0346380 A1    Dec. 1, 2016

Related U.S. Application Data

(60) Provisional application No. 62/167,404, filed on May 28, 2015.

(51) Int. Cl.
*A61K 39/21*    (2006.01)
*A61K 39/42*    (2006.01)
(Continued)

(52) U.S. Cl.
CPC ............. *A61K 39/42* (2013.01); *A61K 39/12* (2013.01); *A61K 45/06* (2013.01); *A61K 48/00* (2013.01);
(Continued)

(58) Field of Classification Search
None
See application file for complete search history.

(56) References Cited

U.S. PATENT DOCUMENTS 4,046,722 A    9/1977 Rowland
4,699,784 A    10/1987 Shih et al.
(Continued)

FOREIGN PATENT DOCUMENTS

WO    8809181    12/1988
WO    9110742    7/1991
(Continued)

OTHER PUBLICATIONS

Abbas et al., Cellular and Molecular Immunology, W.B. Saunders Comp. 1991, p. 43.
(Continued)

*Primary Examiner* — Janet L Andres
*Assistant Examiner* — Stuart W Snyder
(74) *Attorney, Agent, or Firm* — Richard A. Nakashima

(57) ABSTRACT

The present invention concerns methods and compositions for treatment of HIV infection using a T20 expression vector, such as that shown in SEQ ID NO:1 or SEQ ID NO:3. The T20 expression vector may be used in a variety of therapeutic applications, such as ex vivo transfection of dendritic cells to induce a host immune response to HIV, localized transfection in vivo in a gene therapy approach to provide longer term delivery of T20, or in vitro production of T20 peptide. The T20 may be secreted into the circulation to act as a fusion inhibitor of HIV infection, or may induce an endogenous immune response to HIV or HIV-infected cells. Alternatively, a DDD peptide may be incorporated in a fusion protein comprising T20 or another antigenic protein or peptide to enhance the immune response to the protein or peptide.

27 Claims, 5 Drawing Sheets

(51) Int. Cl.
*A61K 45/06* (2006.01)
*A61K 39/12* (2006.01)
*A61K 39/00* (2006.01)
*A61K 48/00* (2006.01)

(52) U.S. Cl.
CPC .. *A61K 2039/5154* (2013.01); *A61K 2039/53* (2013.01); *A61K 2039/55561* (2013.01); *C12N 2740/16134* (2013.01)

(56) References Cited

U.S. PATENT DOCUMENTS

| | | | |
|---|---|---|---|
| 4,868,109 A | 9/1989 | Lansdorp et al. | |
| 5,770,198 A | 6/1998 | Coller et al. | |
| 6,261,537 B1 | 7/2001 | Klaveness et al. | |
| 6,306,393 B1 | 10/2001 | Goldenberg et al. | |
| 6,524,854 B1 | 2/2003 | Monia et al. | |
| 6,706,252 B1 | 3/2004 | Ericsson et al. | |
| 7,060,506 B2 | 6/2006 | Craig | |
| 7,521,056 B2 | 4/2009 | Chang et al. | |
| 7,527,787 B2 | 5/2009 | Chang et al. | |
| 7,534,866 B2 | 5/2009 | Chang et al. | |
| 7,550,143 B2 | 6/2009 | Chang et al. | |
| 7,901,680 B2 * | 3/2011 | Chang | A61K 39/0011 424/134.1 |
| 8,003,111 B2 | 8/2011 | Chang et al. | |
| 8,034,352 B2 | 10/2011 | Chang et al. | |
| 8,158,129 B2 | 4/2012 | Chang et al. | |
| 8,163,291 B2 | 4/2012 | Chang et al. | |
| 8,211,440 B2 | 7/2012 | Chang et al. | |
| 8,246,960 B2 | 8/2012 | Chang et al. | |
| 8,277,817 B2 | 10/2012 | Chang et al. | |
| 8,282,934 B2 | 10/2012 | Chang et al. | |
| 8,349,332 B2 | 1/2013 | Chang et al. | |
| 8,435,540 B2 | 5/2013 | Chang et al. | |
| 8,475,794 B2 | 7/2013 | Chang et al. | |
| 8,481,041 B2 | 7/2013 | Chang et al. | |
| 8,491,914 B2 | 7/2013 | Chang et al. | |
| 8,551,480 B2 | 10/2013 | Chang et al. | |
| 8,562,988 B2 | 10/2013 | Chang et al. | |
| 8,597,659 B2 | 12/2013 | Chang et al. | |
| 8,865,176 B2 | 10/2014 | Chang et al. | |
| 8,871,216 B2 | 10/2014 | Chang et al. | |
| 8,883,160 B2 | 11/2014 | Chang et al. | |
| 8,883,162 B2 | 11/2014 | Chang et al. | |
| 8,906,377 B2 | 12/2014 | Chang et al. | |
| 8,932,593 B2 | 1/2015 | Chang et al. | |
| 2003/0198956 A1 | 10/2003 | Makowski et al. | |
| 2003/0232420 A1 | 12/2003 | Braun et al. | |
| 2004/0018587 A1 | 1/2004 | Makowski et al. | |
| 2004/0126361 A1 | 7/2004 | Saifer et al. | |
| 2004/0241158 A1 | 12/2004 | McBride et al. | |
| 2005/0003403 A1 | 1/2005 | Rossi et al. | |
| 2005/0175619 A1 | 8/2005 | Duffy et al. | |
| 2006/0193865 A1 | 8/2006 | Govindan et al. | |
| 2006/0210475 A1 | 9/2006 | Goldenberg et al. | |
| 2007/0264265 A1 | 11/2007 | Goldenberg et al. | |
| 2009/0111143 A1 | 4/2009 | Goldenberg et al. | |
| 2011/0020273 A1 | 1/2011 | Chang et al. | |
| 2011/0064754 A1 | 3/2011 | Taylor et al. | |
| 2011/0143417 A1 | 6/2011 | Chang et al. | |
| 2011/0158905 A1 | 6/2011 | Goldenberg et al. | |
| 2011/0189083 A1 | 8/2011 | Chang et al. | |
| 2012/0082685 A1 | 4/2012 | Chang et al. | |
| 2012/0196346 A1 | 8/2012 | Chang et al. | |
| 2012/0276100 A1 | 11/2012 | Chang et al. | |
| 2012/0276608 A1 | 11/2012 | Chang et al. | |
| 2013/0078183 A1 | 3/2013 | Chang et al. | |
| 2013/0109073 A1 | 5/2013 | Chang et al. | |
| 2013/0150262 A1 | 6/2013 | Ustav et al. | |
| 2013/0177532 A1 | 7/2013 | Chang et al. | |
| 2013/0217091 A1 | 8/2013 | Chang et al. | |
| 2013/0295005 A1 | 11/2013 | Chang et al. | |
| 2014/0050660 A1 | 2/2014 | Chang et al. | |
| 2014/0099254 A1 | 4/2014 | Chang et al. | |
| 2014/0161766 A1 | 6/2014 | Chang et al. | |
| 2015/0010982 A1 | 1/2015 | Chang et al. | |
| 2015/0023870 A1 | 1/2015 | Chang et al. | |
| 2015/0024458 A1 | 1/2015 | Chang et al. | |
| 2015/0024459 A1 | 1/2015 | Chang et al. | |
| 2015/0050715 A1 | 2/2015 | Chang et al. | |
| 2015/0056680 A1 | 2/2015 | Chang et al. | |

FOREIGN PATENT DOCUMENTS

| | | |
|---|---|---|
| WO | 9111198 | 8/1991 |
| WO | 00/68248 | 11/2000 |
| WO | 2006/107617 | 10/2006 |
| WO | 2006/107786 | 10/2006 |
| WO | 2007/046893 | 4/2007 |
| WO | 2007/075270 | 7/2007 |
| WO | 2015042464 | 3/2015 |

OTHER PUBLICATIONS

Alto et al., "Bioinformatic design of A-kinase anchoring protein-in silico: a potent and selective peptide antagonist of type II protein kinase A anchoring" Proc. Natl. Acad. Sci USA Apr. 15, 2003; 100(8):4445-50.

Backer et al., "Self-Assembled "Dock and Lock" System for Linking Payloads to Targeting Proteins" Bioconjugate Chem., 2006, 17(4):912-919.

Baillie et al., "Compartmentalisation of phospodiesterases and protein kinase A: opposites attract" FEBS Letters 2005; 579:3264-3270.

Banky et al., "Dimerization/Docking Domain of the Type Iα Regulatory Subunit of cAMP-dependent Protein Kinase" J. Biol. Chem. 273:35048-55, 1998.

Basu et al., "Structure-Function Engineering of Interferon-β-1b for Improving Stability, Solubility, Potency, Immunogenicity, and Pharmacokinetic Properties by Site-Selective Mono-PEGylation" Bioconjugate Chem. 2006; 17:618-630.

Belardelli et al., "Interferon-alpha in tumor immunity and immunotherapy" Cytokine Growth Factor Rev. 13(2):119-134 (2002).

Belardelli et al., "International Meeting on Cancer Vaccines: How Can We Enhance Efficacy of Therapeutic Vaccines?" Cancer Res. 64:6827-6830 (2004).

Belardelli et al., "The neglected role of type I interferon in the T-cell response: implications for its clinical use" Immunol. Today 17(8):369-72 (1996).

Biron et al., "Natural killer cells in antiviral defense: function and regulation by innate cytokines" Annu. Rev. Immunol. 17:189-220 (1999).

Brunda et al., "Modulation of Murine Natural Killer Cell Activity in Vitro and in Vivo by Recombinant Human Interferons" Cancer Res. 44:597-601 (1984).

Burns-Hamuro et al., "Distinct interaction modes of an AKAP bound to two regulatory subunit isoforms of protein kinase A revealed by amide hydrogen/deuterium exchange" Protein Science (2005), 14:2982-2992.

Carr et al., "Interaction of the Regulatory Subunit (RII) of cAMP-dependent Protein Kinase with RII-anchoring Proteins Occurs through an Amphipathic Helix Binding Motif" J. Biol. Chem. 266:14188-92 (1991).

Carr et al., "Identification of Sperm-specific Proteins That Interact with A-kinase Anchoring Proteins in a Manner Similar to the Type II Regulatory Subunit of PKA" J. Biol. Chem. 276(20):17332-17338 (2001).

Carrero et al., "Lymphocytes are detrimental during the early innate immune response against Listeria monocytogenes" J. Exp. Med. 203(4):933-940 (2006).

Chang et al., "The Dock and Lock Method: A Novel Platform Technology for Building Multivalent, Multifunctional Structures of Defined Composition with Retained Bioactivity" Clin. Cancer Res. Sep. 15, 2007;13(18 Suppl), pp. 5586-5591.

Chmura et al., "Antibodies with infinite affinity" Proc. Natl. Acad. Sci. USA 98(15):8480-8484 (2001).

(56) References Cited

OTHER PUBLICATIONS

Colledge et al., "AKAPs: from structure to function" Trends Cell Biol. 6:216-21 (1999).
Corbin et al., "Regulation of Adenosine 3',5'-Monophosphate-dependent Protein Kinase" J. Biol. Chem. 248:1813-21 (1973).
Dhalluin et al., "Structural and Biophysical Characterization of the 40 kDa PEG-Interferon-α2a and Its Individual Positional Isomers" Bioconjugate Chem. 2005;16:504-517.
Dodart et al., "Immunotherapy for Alzheimer's Disease: will vaccination work?" Trends Mol. Med. 9(3):85-87 (2003).
Doherty et al., "Site-Specific PEGylation of Engineered Cysteine Analogues of Recombinant Human Granulocyte-Macrophage Colony-Stimulating Factor" Bioconjugate Chem. 2005;16:1291-1298.
Ferrantini et al., "IFN-α1 Gene Expression into a Metastatic Murine Adenocarcinoma (TS/A) Results in CD8+ T Cell-Mediated Tumor Rejection and Development of Antitumor Immunity" J. Immunol. 153:4604-15 (1994).
Ferrantini et al., "Interferon-α and cancer: Mechanisms of action and new perspectives of clinical use" Biochimie 89: 884-893 (2007).
Foser et al., "Improved biological and transcriptional activity of monopegylated interferon-α-2a isomers" The Pharmacogenomics J 3:312-319 (2003).
Gillies et al., "High-level expression of chimeric antibodies using adapted cDNA variable region cassettes" J. Immunol. Methods 125 (1989) 191-202.
Glennie et al., "Mechanisms of killing by anti-CD20 monoclonal antibodies" Mol. Immunol. 44:3823-3837 (2007).
Gold et al., "A Novel Bispecific, Trivalent Antibody Construct for Targeting Pancreatic Carcinoma", Cancer Res. 68:4819-26, 2008.
Gold et al., "Molecular Basis of AKAP Specificity for PKA Regulatory Subunits" Mol. Cell Nov. 3, 2006;24(3):383-95.
Goldenberg et al., "Multifunctional Antibodies by the Dock-and-Lock Method for Improved Cancer Imaging and Therapy by Pretargeting" J. Nucl. Med. 49:158-63, 2008.
Goldenberg et al., "Properties and structure-function relationships of veltuzumab (hA20), a humanized anti-CD20 monoclonal antibody" Blood 113:1062-70 (2009).
Goodson et al., "Site-Directed PEGylation of Recombinant Interleukin-2 at its Glycosylation Site" Nat. Biotechnology Apr. 1990;8(4):343-6.
Grace et al., "Site of Pegylation and Polyethylene Glycol Molecule Size Attenuate Interferon-α Antiviral and Antiproliferative Activities through the JAK/STAT Signaling Pathway" J. Biol. Chem. 2005;280(8):6327-6336.
Grimley et al., "Prolonged STAT1 Activation Related to the Growth Arrest of Malignant Lymphoma Cells by Interferon-α" Blood 91(8):3017-27 (1998).
Gutterman et al., "Leukocyte Interferon-Induced Tumor Regression in Human Metastatic Breast Cancer, Multiple Myeloma, and Malignant Lymphoma" Ann. Intern. Med. 93(3):399-406 (1980).
Gutterman et al., "Cytokine therapeutics: Lessons from interferon α" Proc. Natl. Acad. Sci. USA 91:1198-205 (1994).
Harris et al., "Effect of pegylation on pharmaceuticals" Nat. Rev. Drug. Discov. 2:214-221 (2003).
Hausken et al., "Mutational Analysis of the A-Kinase Anchoring Protein (AKAP)-binding Site on RII" J. Biol. Chem. 271:29016-22 (1996).
Hodneland et al., Selective immobilization of proteins to self-assembled monolayers presenting active site-directed capture ligands, Proc. Natl. Acad. Sci. USA 2002; 99:5048-5052.
Huang et al., "Targeting IFN-α to B Cell Lymphoma by a Tumor-Specific Antibody Elicits Potent Antitumor Activities" J. Immunol. 179:6881-88 (2007).
Hundsrucker et al., "High-affinity AKAP7δ-protein kinase A interaction yields novel protein kinase A-anchoring disruptor peptides" Biochem. J. (2006) 396, 297-306.
Kimby et al., "Long-term molecular remissions in patients with indolent lymphoma treated with rituximab as a single agent or in combination with interferon alpha-2a: A randomized phase II study from the Nordic Lymphoma Group" Leuk. Lymphoma 49(1)102-112 (2008).
Kinderman et al., "A Dynamic Mechanism for AKAP Binding to RII Isoforms of cAMP-Dependent Protein Kinase" Mol. Cell 24(3):397-408 (2006).
Kinstler et al., "Characterization and Stability of N-terminally PEGylated rhG-CSF" Pharm. Res. 1996;13 (7):996-1002.
Kramer et al., "Cell and virus sensitivity studies with recombinant human alpha interferons" J. Interferon. Res. 3 (4):425-35 (1983).
Le Bon et al., "Type I Interferons Potently Enhance Humoral Immunity and Can Promote Isotype Switching by Stimulating Dendritic Cells In Vivo" Immunity 14:461-470 (2001).
Lee et al., "Solid-Phase PEGylation of Recombinant Interferon α-2a for Site-Specific Modification: Process Performance, Characterization, and in Vitro Bioactivity" Bioconjugate Chem. 2007; 18:1728-34.
Lohmann et al., "High-affinity binding of the regulatory subunit (RII) of cAMP-dependent protein kinase to microtubule-associated and other cellular proteins" Proc. Natl. Acad. Sci. USA 81:6723-27 (1984).
Luft et al., "Type I IFNs Enhance the Terminal Differentiation of Dendritic Cells" J. Immunol. 161:1947-1953 (1998).
Mason, Anthony J., "Functional Analysis of the Cysteine Residues of Activin A" Mol. Endocrinol. 8:325-32 (1994).
Armbruster et al., "Passive immunization with the anti-HIV-1 human monoclonal antibody (hMAb) 4E10 and the hMAb combination 4E10/2F5/2G12", J Antimicrob Chemother. Nov. 2004;54(5):915-20.
Backstrom et al., Characterization of an internal permissive site in the cholera toxin B-subunit and insertion of epitopes from human immunodeficiency virus-1, hepatitis B virus and enterotoxigenic *Escherichia coli*, Gene. Nov. 20, 1995;165(2):163-71.
Barretina et al., "Anti-HIV-1 activity of enfuvirtide (T-20) by inhibition of bystander cell death", Antivir Ther. Apr. 2003;8(2):155-61.
Bergamini et al., "Adriamycin selectively inhibits HIV replication in resting macrophages", Int Conf AIDS. Jun. 16-21, 1991; 7:109 (Abstract No. W.A.1071).
Berry et al., "Structure of an anti-HIV monoclonal Fab antibody fragment specific to a gp120 C-4 region peptide", Proteins. Nov. 15, 2001;45(3):281-2.
Brave et al., "A new multi-clade DNA prime/recombinant MVA boost vaccine induces broad and high levels of HIV-1-specific CD8(+) T-cell and humoral responses in mice", Mol Ther. Sep. 2007;15(9):1724-33.
Brave et al., "Multigene/multisubtype HIV-1 vaccine induces potent cellular and humoral immune responses by needle-free intradermal delivery", Mol Ther. Dec. 2005;12(6):1197-205.
Broliden et al., "A monoclonal antibody to human immunodeficiency virus type 1 which mediates cellular cytotoxicity and neutralization", J Virol. Feb. 1990;64(2):936-40.
Bryson et al., "Cross-neutralizing human monoclonal anti-HIV-1 Antibody 2F5: preparation and crystallographic analysis of the free and epitope-complexed forms of its Fab' fragment", Protein and Peptide Letters, vol. 8, No. 5, pp. 413-418, 2001; Bentham Science Publishers Ltd.
Cardillo et al., "Targeting both IGF-1R and mTOR synergistically inhibits growth of renal cell carcinoma in vitro", BMC Cancer. Apr. 1, 2013;13:170.
Chang et al., "A new method to produce monoPEGylated dimeric cytokines shown with human interferon-α2b", Bioconjug Chem. Oct. 21, 2009;20(10):1899-907.
Chang et al., "A novel class of anti-HIV agents with multiple copies of enfuvirtide enhances inhibition of viral replication and cellular transmission in vitro", PLoS One. 2012;7(7):e41235.
Chang et al., "Evaluation of a novel hexavalent humanized anti-IGF-1R antibody and its bivalent parental IgG in diverse cancer cell lines", PLoS One. 2012;7(8):e44235.
Golay et al., "Mechanism of action of therapeutic monoclonal antibodies: promises and pitfalls of in vitro and in vivo assays", Arch Biochem Biophys. Oct. 15, 2012;526(2):146-53.

(56) References Cited

OTHER PUBLICATIONS

Heath et al., "Aggresomes resemble sites specialized for virus assembly", J Cell Biol. Apr. 30, 2001;153(3):449-55.
Johansson et al., "Elimination of HIV-1 infection by treatment with a doxorubicin-conjugated anti-envelope antibody", AIDS. Oct. 3, 2006;20(15):1911-5.
Johansson et al., "Intracellular targeting of CEA results in Th1-type antibody responses following intradermal genetic vaccination by a needle-free jet injection device", ScientificWorldJournal. Jun. 12, 2007;7:987-99.
Johnston et al., "Aggresomes: a cellular response to misfolded proteins", J Cell Biol. Dec. 28, 1998;143(7):1883-98.
Jubala et al., "CD20 expression in normal canine B cells and in canine non-Hodgkin lymphoma", Vet Pathol. Jul. 2005;42(4):468-76.
Lund et al., "Signal sequence deletion and fusion to tetanus toxoid epitope augment antitumor immune responses to a human carcinoembryonic antigen (CEA) plasmid DNA vaccine in a murine test system", Cancer Gene Ther. May 2003;10(5):365-76.
Matthews et al., "Prospects for development of a vaccine against HTLV-III-related disorders", AIDS Res Hum Retroviruses. 1987;3 Suppl 1:197-206.
Nilsson et al., "HIV-DNA Given with or without Intradermal Electroporation Is Safe and Highly Immunogenic in Healthy Swedish HIV-1 DNA/MVA Vaccinees: A Phase I Randomized Trial", PLoS One. Jun 29, 2015;10(6):e0131748.
Paulik et al., "Drug-antibody conjugates with anti-HIV activity", Biochem Pharmacol. Dec. 1, 1999;58(11):1781-90.
Prlic et al., "Immunology. An antibody paradox, resolved.", Science. Mar. 31, 2006;311(5769):1875-6.
Rachlis et al., "Guidelines for antiretroviral therapy for HIV infection. Canadian HIV Trials Network Antiretroviral Working Group", CMAJ. Feb. 24, 1998;158(4):496-505.
Sato et al., "Intergration of cell experiment system", KAST Annual Research Report, 2003 (Abstract).
Schonning et al., "Rapid selection for an N-linked oligosaccharide by monoclonal antibodies directed against the V3 loop of human immunodeficiency virus type 1", J Gen Virol. Apr. 1996;77 ( Pt 4):753-8.
Wileman et al., "Aggresomes and autophagy generate sites for virus replication", Science. May 12, 2006;312 (5775):875-8.
Liu et al., "Trop-2-targeting tetrakis-ranpirnase has potent antitumor activity against triple-negative breast cancer", Mol Cancer. Mar. 10, 2014;13:53.
Matarrese et al., "Type I Interferon Gene Transfer Sensitizes Melanoma Cells to Apoptosis via a Target Activity on Mitochondrial Function" Am. J. Pathol. 2002, 160(4):1507-1520.
Mecchia et al., "Type I consensus interferon (CIFN) gene transfer into human melanoma cells up-regulates p53 and enhances cisplatin-induced apoptosis: implications for new therapeutic strategies with IFN-alpha" Gene Ther. (2000) 7, 167-179.
Newlon et al., "A Novel Mechanism of PKA Anchoring Revealed by Solution Structures of Anchoring Complexes" EMBO J. 2001; 20:1651-1662.
Newlon et al., "The molecular basis for protein kinase A anchoring revealed by solution NMR" Nature Struct. Biol. 1999; 3:222-227.
Ngo et al., "Computational Complexity, Protein Structure Prediction, and the Levinthal Paradox", The Protein Folding Problem and Tertiary Structure Prediction, Ch. 14, pp. 492-495, (Mertz & Le Grand, Eds.), Birkhauser Boston, 1994.
Osborn et al., "Pharmacokinetic and Pharmacodynamic Studies of a Human Serum Albumin-Interferon-α Fusion Protein in Cynomolgus Monkeys" J. Pharmacol. Exp. Ther. 303(2):540-548 (2002).
Oyen et al., "Human testis cDNA for the regulatory subunit RIIα of cAMP-dependent protein kinase encodes an alternate amino-terminal region" FEBS Letters 246:57-64, 1989.
Ozzello et al., "Conjugation of interferon alpha to a humanized monoclonal antibody (HuBrE-3vl) enhances the selective localization and antitumor effects of interferon in breast cancer xenografts" Breast Cancer Res. Treat. 48:135-147 (1998).
Paquette et al., "Interferon-α and granulocyte-macrophage colony-stimulating factor differentiate peripheral blood monocytes into potent antigen-presenting cells" J. Leukoc. Biol. 64:358-367; 1998.
Pelham et al., "Interferon-α conjugation to human osteogenic sarcoma monoclonal antibody 791T/36" Cancer Immunol. Immuother 1983;15(3):210-216.
Pepinsky et al., "Improved Pharmacokinetic Properties of a Poly-ethylene Glycol-Modified Form of Interferon-β-1a with Preserved in Vitro Bioactivity" Pharmacol. Exp. Ther. 2001; 297(3):1059-1066.
Pilling et al., "Interferon-β mediates stromal cell rescue of T cells from apoptosis" Eur. J. Immunol. 29:1041-1050 (1999).
Rabjohn et al., "Molecular Cloning and Epitope Analysis of the Peanut Allergen Ara h 3" J. Clinical Investigation 103(4):535-542 (1999).
Raefsky et al., "Studies of Interferon as a regulator of hematopoietic cells proliferation" J. Immunol. 135(4):2507-2512 (1985).
Rose et al., "Structural basis of dimerization, coactivator recognition and MODY3 mutations in HNF-1α" Nature Struct. Biol. 2000; 7:744-748.
Rosendahl et al., "A Long-Acting, Highly Potent Interferon α-2 Conjugate Created Using Site-Specific PEGylation" Bioconjugate Chem. 2005;16:200-207.
Rossi et al., "A New Class of Hexavalent Bispecific Antibodies and Immunocytokines with Enhanced Pharmacokinetics and Improved Efficacy in Vivo", Blood (ASH Annual Meeting Abstracts) 2012 120: Abstract 2451.
Rossi et al., "Novel Designs of Multivalent Anti-CD20 Humanized Antibodies as Improved Lymphoma Therapeutics" Cancer Res. 68:8384-92 (2008).
Rossi et al., "Stably tethered multifunctional structures of defined composition made by the dock and lock method for use in cancer targeting" Proc. Natl. Acad. Sci. Epub Apr. 24, 2006, vol. 103, No. 18, pp. 6841-6846.
Rossi et al., "The dock-and-lock method combines recombinant engineering with site-specific covalent conjugation to generate multifunctional structures", Bioconjug Chem. Mar. 21, 2012;23(3):309-23.
Rossi et al., "Complex and defined biostructures with the dock-and-lock method", Trends Pharmacol Sci. Sep. 2012;33(9):474-81.
Rossi et al., "Optimization of multivalent bispecific antibodies and immunocytokines with improved in vivo properties", Bioconjug Chem. Jan. 16, 2013;24(1):63-71.
Rossi et al., "A new class of bispecific antibodies to redirect T cells for cancer immunotherapy", MAbs. Mar.-Apr. 2014;6(2):381-91.
Rossi et al., "Hexavalent bispecific antibodies represent a new class of anticancer therapeutics: 1. Properties of anti-CD20/CD22 antibodies in lymphoma", Blood. Jun. 11, 2009;113(24):6161-71.
Rustandi et al., "The Ca2+-Dependent Interaction of S100B(ββ) with a Peptide Derived from p53", Biochemistry 1998; 37: 1951-1960.
Sabaawy et al., "Enhancement of 5-fluorouracil cytotoxicity on human colon cancer cells by retrovirus-mediated Interferon-α gene transfer" Int. J. Oncol. Jun. 1999; 14(6):1143-51.
Salles et al., "Rituximab combined with chemotherapy and interferon in follicular lymphoma patients: results of the GELA-GOELAMS FL2000 study" Blood 2008; 112:4824-4831.
Santini et al., "Type I Interferon as a Powerful Adjuvant for Monocyte-derived Dendritic Cell Development and Activity In Vivo and in Hu-PBL-SCID Mice" J. Exp. Med. 191(10):1777-1788 (2000).
Scott et al., "Type II Regulatory Subunit Dimerization Determines the Subcellular Localization of the cAMP-dependent Protein Kinase" J. Biol. Chem. 265:21561-66 (1990).
Scott et al., "Cyclic nucleotide-dependent protein kinases" Pharmacol. Ther. 1991;50(1):123-45.
Seffernick et al., "Melamine Deaminase and Atrazine Chlorohydrolase: 98 Percent Identical but Functionally Different" J. Bacteriol. 183(8):2405-2410 (2001).

(56) References Cited

OTHER PUBLICATIONS

Sharkey et al., "Improved Therapeutic Results by Pretargeted Radioimmunotherapy of Non-Hodgkin's Lymphoma with a New Recombinant, Trivalent, Anti-CD20, Bispecific Antibody" Cancer Res. 68:5282-90 (2008).

Sharkey et al., "Metastatic Human Colonic Carcinoma: Molecular Imaging with Pretargeted SPECT and PET in a Mouse Model" Radiology 246:497-507 (2008).

Sharkey et al., "Improved cancer therapy and molecular imaging with multivalent, multispecific antibodies", Cancer Biother Radiopharm. Feb. 2010;25(1):1-12.

Sidky et al., "Inhibition of Angiogenesis by Interferons: Effects on Tumor- and Lymphocyte-induced Vascular Responses" Cancer Res. 47:5155-5161, Oct. 1, 1987.

Stancovski et al., "Mechanistic aspects of the opposing effects of monoclonal antibodies to the ERBB2 receptor on tumor growth", Proc Natl Acad Sci U S A. Oct. 1, 1991;88(19):8691-5.

Stein et al., "Characterization of a New Humanized Anti-CD20 Monoclonal Antibody, IMMU-106, and Its Use in Combination with the Humanized Anti-CD22 Antibody, Epratuzumab, for the Therapy of Non-Hodgkin's Lymphoma" Clin. Cancer Res. vol. 10, 2868-2878, Apr. 15, 2004.

Stein et al., "Characterization of a humanized IgG4 anti—HLA-DR monoclonal antibody that lacks effector cell functions but retains direct antilymphoma activity and increases the potency of rituximab" Blood 2006;108:2736-2744.

Stokka et al., "Characterization of A-kinase-anchoring disruption using a solution-based assay" Biochem. J. (2006) 400, 493-499.

Stryer et al., "Levels of Structure in Protein Architecture", Biochemistry, 3rd Ed., pp. 31-33, W.H. Freeman & Co., New York, 1988.

Takaoka et al., "Integration of interferon-α/β signalling to p53 responses in tumour suppression and antiviral defence" Nature Jul. 31, 2003;424(6948):516-23.

Taylor, S., "cAMP-dependent Protein Kinase" J. Biol. Chem. 1989;264(15):8443-8446.

Walsh et al., "An Adenosine 3', 5'-Monophosphate-dependant Protein Kinase from Rabbit Skeletal Muscle" J. Biol. Chem. 243(13):3763-3774 (1968).

Weck et al., "Comparison of the Antiviral Activities of Various Cloned Human Interferon-α Subtypes in Mammalian Cell Cultures" J. Gen. Virol. (1981), 57, 233-237.

Winkler et al., "Changing the Antigen Binding Specificity by Single Point Mutations of an Anti-p24 (HIV-1) Antibody" J. Immunol. 165:4505-14 (2000).

Witkowski et al., "Conversion of a α-Ketoacyl Synthase to a Malonyl Decarboxylase by Replacement of the Active-Site Site Cysteine with Glutamine" Biochemistry 38(36):11643-50 (1999).

Wong et al., "AKAP Signalling Complexes: Focal Points in Space and Time" Nat. Rev. Mol. Cell Biol. 12:959-70 (2004).

Yu et al., "Interaction between bevacizumab and murine VEGF-A: a reassessment", Invest Ophthalmol Vis Sci. Feb. 2008;49(2):522-7.

Zhu et al., "Inhibition of tumor growth and metastasis by targeting tumor-associated angiogenesis with antagonists to the receptors of vascular endothelial growth factor" Invest. New Drugs 17:195-212, 1999.

\* cited by examiner

*FIG. 3*

GGCGGCCACATCCAGATCCCGCTGGGGCTCACGGAGCTGCAGGGCTGCAGGGCTACACGGTGGAGGTGCTGCGAGACAGCAGCCG
CCTGACCTCGTCGAATTCGCAGTGGAGTACTTCACCCGCCTGAGAGAAGCTGCGCCTGAGTTCCCTAAACCCAGCACTCC
ACCCGGATCTTCCGGCACCACCACCACCACGGATCCTATACCAGCCTGATTCATAGCCTGATTGAAGAAAGCCAG
AACCAGCAGGAAAAACGAACAGGAACTGCTGGAACTGGATAAATGGGCGAGCCTGTGAACTGGTTTTGACTCGAGCACCA
CCACCACCACCACTGAGATCCGGCTAACAAAGCCCGAAAAGGAAGCTGAGTTGGCTGCTGCCACCGCTGCAGCAATAACTAG
CATAACCCCTGGGCCTCTAAACGGGTCTTGAGGGGTTTTTGCTGAAAGGAGGAACTATATCCGGAT (SEQ ID NO: 3)

T20 CONSTRUCTS FOR ANTI-HIV (HUMAN IMMUNODEFICIENCY VIRUS) THERAPY AND/OR VACCINES

RELATED APPLICATIONS

This application claims the benefit under 35 U.S.C. 119(e) of U.S. Provisional Patent Application 62/167,404, filed May 28, 2015, the text of which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on May 19, 2016, is named IMM360US1_SL.txt and is 14,349 bytes in size.

BACKGROUND OF THE INVENTION

Field of the Invention

The present invention concerns methods and compositions for treating human immunodeficiency virus (HIV), either prophylactically or post-infection. The compositions and methods relate to a T20 minicircle or vaccines comprising a T20 minicircle. A novel T20 minicircle construct is provided, comprising the nucleic acid sequence of SEQ ID NO:1. The T20 minicircle may be used for anti-HIV therapy (e.g., enfuvirtide), gene therapy or viral eradication in infected hosts, or for production of anti-HIV vaccines or vaccine enhancement in non-infected hosts. T20 may be used alone or in combination with one or more anti-HIV agents, as discussed below. In some embodiments T20 may be expressed as an unconjugated peptide. Alternatively a fusion protein or peptide comprising T20 attached to another therapeutic peptide may be used. All such peptide products may be expressed from a minicircle as disclosed herein, or the minicircle itself may be utilized for therapeutic purposes. Enfuvirtide has been used for salvage therapy in patients with multi-drug resistant HIV, alone or in combination with other anti-viral agents. In certain embodiments, adjuvant agents may be utilized to increase the immune response to T20 or other antigens. An exemplary antigen is a DDD (dimerization and docking domain) peptide, as disclosed herein.

Description of Related Art

Minicircles are episomal DNA vectors that are produced as small (~4 kb) circular expression cassettes, derived from plasmids but devoid of any prokaryotic DNA (see, e.g., Wikipedia "Minicircle"). Minicircles have been used as transgene carriers for genetic modification of mammalian cells (Id.). Their smaller molecular size enables more efficient transfections and offers sustained expression over a period of weeks as compared to standard plasmid vectors that only work for a few days (see, e.g., Kay et al., 2010, Nature Biotech 28:1287-89). Thus, minicircles may be used for direct transfection of host cells, or may be used for production of cloned peptides which in turn may be used as therapeutic agents and/or for vaccination. Since minicircles contain no bacterial DNA sequences, they are less likely to be recognized by the host immune system and destroyed (Argyros et al., 2011, J Mol Med (Berlin) 89:515-29). They are therefore more suitable for in vivo use than standard expression systems, although performance for in vitro use is also improved (Argyros et al., 2011, J Mol Med (Berlin) 89:515-29).

Minicircle production typically involves production of a "parental plasmid" and induction of the activity of a site-specific recombinase to excise the prokaryotic vector sequences (Chen et al., 2003, Mol Ther 8:495-500). The resulting minicircles may be recovered by a variety of techniques. Early versions of minicircles lacked an origin of replication and were therefore lost as cell division occurred. More recently, self-replicating minicircles comprising an S/MAR (scaffold/matrix attachment region) element have been designed (e.g., Argyros et al., 2011, J Mol Med 89:515-29). Self-replicating minicircles may allow prolonged peptide expression from transfected cells. A need exists for improved minicircle vectors for more effective therapeutic use.

T20 (enfuvirtide) is the first HIV fusion inhibitor approved for therapeutic human use (Morris & Kraus, 2005, J Pediatr Pharmacol Ther 10:215-470. HIV-1 infection is initiated by binding of the gp120 envelope protein to its CD4 cell surface receptor and a coreceptor (CXCR4 or CCR5) (Martinez-Munoz et al., 2014, Proc. Natl Acad Sci USA 111:E1960-69). Binding of gp120 is followed by the release of and conformation changes in the associated viral transmembrane gp41 subunit, which is required for membrane fusion with the host cell (Cai et al., 2011, Curr Top Med Chem 11:2959-84). Enfuvirtide works by targeting a conformational transition in gp41, preventing creation of an entry pore for the viral capsid (Cai et al., 2011, Curr Top Med Chem 11:2959-84). Because it is a peptide with poor oral availability, enfuvirtide is typically administered by subcutaneous injection, after reconstitution by the patient. Due to the chronic nature of the treatment, the difficulty of administration contributes to poor patient compliance (Home et al., 2009, AIDS Res Ther 6:2). A need exists for better T20 vectors that will allow improved means of T20 administration.

SUMMARY OF THE INVENTION

The present invention fulfills an unresolved need in the art by providing T20 minicircle (MC) expression vectors, encoding the production of the T20 HIV fusion inhibitor. An exemplary T20 minicircle DNA sequence is shown in SEQ ID NO:1. The amino acid sequence of T20 is provided in SEQ ID NO:2. The MC construct exhibits several advantages compared to traditional expression vectors that comprise substantial amounts of prokaryotic nucleic acid sequences, such as decreased immunogenicity, a lower potential for inducing host immune response, greater stability of the construct in host cells, prolonged expression and increased production of T20 peptide.

The T20 MC constructs are of use for prevention of HIV infection, for example as components of vaccines or vaccine adjuncts, or for treatment of existing HIV infection, for example by administration of expressed T20 peptide or by incorporation of a T20 MC expression vector into host cells for protein expression in vivo.

The T20 peptide or T20 MC vector may be used alone or in combination with one or more other known anti-HIV agents, selected from the group consisting of fusion inhibitors (e.g., enfuvirtide, maraviroc), integrase inhibitors (e.g. raltegravir, elvitegravir, dolutegravir), reverse transcriptase inhibitors (e.g., KRV2110, zidovudine, abacavir, emtricitabine, tenofovir, etravirine, rilpivirine, didanosine, zalcitabine, lamivudine, stavudine, nevirapine, efavirenz), protease inhibitors (e.g., saqujinavir, indinavir, ritonavir, lopinavir, nelfinavir, amprenavir, darunavir, atazanavir) and anti-HIV antibodies or other binding molecules (e.g., P4/D10, 2G12, 2F5, 4E10, Hippeastrum hybrid agglutinin (HHA)). Combination therapy with T20 (enfuvirtide) has been reported to decrease viral load to below-detectable levels in as many as 90 to 95% of treated patients (see, e.g., McGillick et al., 2010, Biochem 49:3575-92). It is generally acknowledged that combination therapy is more effective than single agent therapy in controlling HIV infection and preventing development of drug-resistant HIV (Jenabian et al., 2009, J Antimicrob Chemother 64:1192-95). Many anti-HIV therapeutic agents are known in the art and any such known agent may be used.

Use of such combination therapies may block or prevent infection of cells with HIV, may reduce or eliminate HIV-infected cells in the patient, and/or may reduce or eliminate residual foci of HIV-infected cells in patients treated previously and/or simultaneously with other known anti-retroviral therapies.

Other embodiments relate to use of T20 minicircles for gene therapy, as discussed in detail below. Still other embodiments concern T20 minicircles as components of vaccines. In certain embodiments, the use of T20 or other antigens in vaccines may be enhanced by use of an adjuvant agent. In a specific embodiment, the adjuvant may be a DDD moiety (e.g, SEQ ID NO:5).

BRIEF DESCRIPTION OF THE DRAWINGS

The following drawings form part of the present specification and are included to further demonstrate certain aspects of particular embodiments of the invention. The embodiments may be better understood by reference to one or more of these drawings in combination with the detailed description presented herein.

FIG. 3 shows a different T20 nucleic acid sequence (SEQ ID NO:3), incorporating a DDD2 moiety (underlined), hinge linker (italic), (His)$_6$GS (SEQ ID NO: 16) (bold), and T20 (underlined and italic).

DESCRIPTION OF ILLUSTRATIVE EMBODIMENTS

Figure 1:
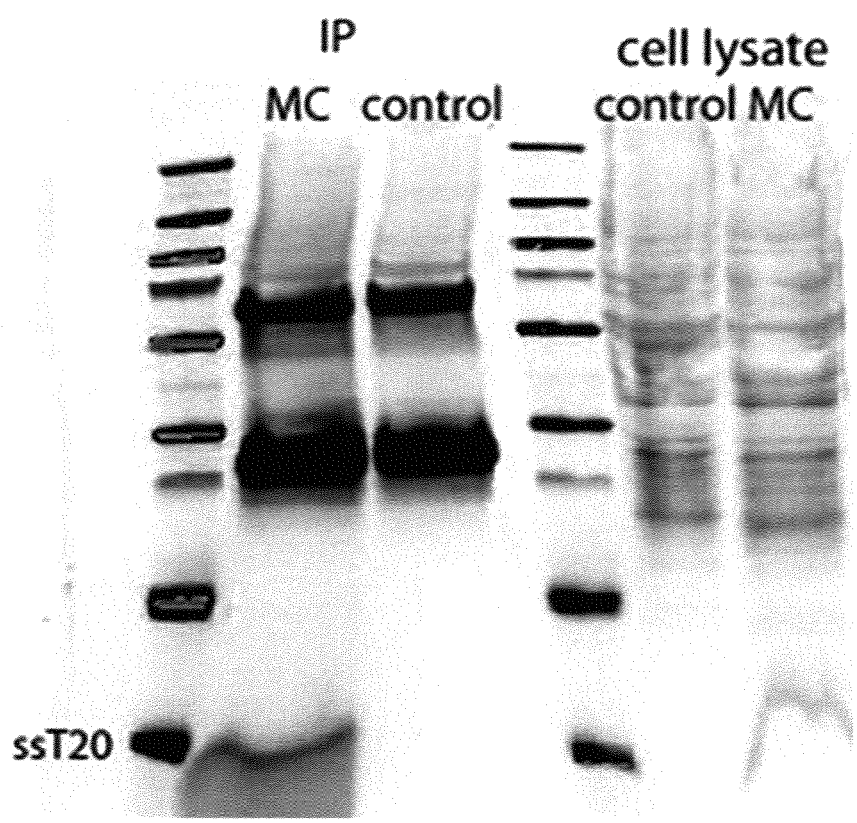
FIG. 1 discloses expression of T20 peptide from MC vector in vitro. A western blot was performed on immunoprecipitated (IP) peptide and cell lysate from HeLa cells transfected with MC or untransfected (control).

All documents, or portions of documents, cited in this application, including but not limited to patents, patent applications, articles, books, and treatises, are hereby expressly incorporated by reference in their entirety.

DEFINITIONS

As used herein, "a" or "an" may mean one or more than one of an item.

As used herein, the terms "and" and "or" may be used to mean either the conjunctive or disjunctive. That is, both terms should be understood as equivalent to "and/or" unless otherwise stated.

As used herein, "about" means within plus or minus ten percent of a number. For example, "about 100" would be mean any number between 90 and 110.

As used herein, "minicircle" refers to a small (4 kb or less), circular, double-stranded, episomal expression vector that is derived from a plasmid by an inducible recombinase, but that is devoid of any prokaryotic DNA. Minicircles may or may not be self-replicating, for example by incorporation of an S/MAR element.

As used herein, "lipopolysaccharide" refers to large molecules that comprise a lipid and a polysaccharide joined by a covalent bond. Lipopolysaccharides are generally found in the outer membrane of Gram-negative bacteria. Lipopolysaccharides of use include those that act as endotoxins and/or elicit strong immune responses in a host.

A "therapeutic agent" is an atom, molecule, or compound that is useful in the treatment of a disease. Examples of therapeutic agents include antibodies, antibody fragments, drugs, virostatic agents, toxins, enzymes, nucleases, hormones, immunomodulators, antisense oligonucleotides, small interfering RNA (siRNA), chelators, boron compounds, photoactive agents, dyes, and radioisotopes. Other exemplary therapeutic agents and methods of use are disclosed in U.S. Patent Application Publication Nos. 20050002945, 20040018557, 20030148409 and 20050014207, each incorporated herein by reference.

The term "pDNA" refers to plasmid DNA.

T20 Fusion Inhibitor Peptide

Some viruses, most notably HIV, must undergo a complex process of fusion with the host cell membrane in order to enter the host cell and reproduce (e.g., U.S. Publ. No. 20040049018). In the case of HIV, the outer membrane of the HIV virus fuses with the cell membrane of CD4+ T cells during reproduction (U.S. Publ. No. 20040049018). T20 is the first member of the class of antiviral fusion inhibitors to receive FDA approval for human use. As a result of T20 administration, the reproduction of HIV is blocked and resultant death of the CD4+ T cells does not occur (U.S. Publ. No. 20040049018).

Data from two large, internationally conducted Phase III trials indicated that combination therapy with T-20 reduced HIV to undetectable levels in the blood in at least twice the percentage of patients and provided an improved immune response at 24 weeks, as compared to those who took combination therapy without T-20 (U.S. Publ. No. 20040049018). Additionally, those receiving T-20 were less likely to experience virological failure or relapse over 24 weeks (U.S. Publ. No. 20040049018).

Viral resistance to currently approved anti-HIV drugs is a significant issue in the clinical management of HIV today. Many patients who begin combination antiretroviral treatment with currently approved medications will develop resistance to one or more of these agents over time. Research suggests, however, that T20 may be unaffected by resistance to any of the currently approved antiretroviral classes (U.S. Publ. No. 20040049018).

By virtue of its peptide nature, enfuvirtide is marketed in lyophilised form, which must be reconstituted by the patient and self-administered twice daily by subcutaneous injection. Due to the chronic nature of this kind of therapy, this dosage form may be a major problem for the patient's adherence to this drug regimen. The present invention avoids the requirement for daily subcutaneous self-administration by the patient, by providing a minicircle form of T20 expression vector as described below. Once the T20 MC has been transfected or otherwise introduced into host cells, the relative stability of the minicircle design allows for long-term exposure to T20 peptide, without the need for repetitive and frequent administration.

The T20 MC construct disclosed herein may be used for T20 peptide production in vitro in cultured cells, or may alternatively be transfected or otherwise introduced into host cells, which then express and secrete T20 into the circulation in vivo in a gene therapy approach, described in more detail below. T20 produced in vitro may be used in the same methods and compositions in current therapeutic use for enfuvirtide (FUZEON®).

T20 Vaccines

The use of dendritic cell (DC) based vaccines has been disclosed (see, e.g., U.S. Publ. No. 20110182937, filed Jan. 21, 2011, the Figures and Examples section incorporated herein by reference). Dendritic cells may be isolated by standard techniques, and loaded with an antigen-encoding vector by transfection or lipofection (U.S. Publ. No. 20110182937; Fong & Engleman, 2000, *Dendritic Cells in Cancer Immunotherapy*. Ann Rev Immunol). Expression of the cloned protein or peptide in the DCs induces an immune response to the protein or peptide antigen. In certain embodiments, the T20 MC vector may be loaded into a patient's isolated DCs (or allogeneic DCs) and the loaded DCs administered to the patient (e.g., Kundu et al., 2009, AIDS Research and Human Retroviruses 14:551-60). Because the T20 sequence mimics a portion of the C-terminal heptad repeat 2 (HR2) region of native gp41 that is expressed in HIV, administration of DCs transfected with T20 MC is effective to induce an immune response against gp41 and HIV, which is of use to reduce or eliminate the virus.

In alternative embodiments, the vaccine efficacy may be improved, for example by use of adjunct compounds such as GM-CSF and/or interferon-α2b (U.S. Publ. No. 20110182937). A blood sample from a patient (or allogeneic subject) may be used to isolate monocytes, for example by elutriation. The monocytes may then be cultured in medium comprising GM-CSF and/or interferon-α2b, before the activated DCs are loaded with T20 MC. After antigen loading and activation, the DC vaccine may be harvested at approximately 72 hours, washed by centrifucation and resuspended. In certain embodiments, the vaccine may be stored in freezing solution, consisting of 80% PlasmaLyte, 10% human serum albumin (HSA), and 10% DMSO. Aliquots of the cell suspension may be filled into glass vaccine vials and frozen, prior to administration.

Expression of T20 peptide in the DCs is effective to induce the host immune system to respond to HIV. In other alternative embodiments, the DCs may be further activated by exposure to lipopolysaccharide (U.S. Publ. No. 20110182937). The vaccine therapy may be utilized alone, or in combination with anti-retroviral therapy such as HAART, protease inhibitors, reverse transcriptase inhibitors, or anti-HIV antibodies.

The vaccines are administered in a manner compatible with the dosage formulation, and in such amount as will be therapeutically effective and immunogenic. The quantity to be administered depends on the subject to be treated, including, e.g., the capacity of the individual's immune system to generate an immune response. Precise amounts of cells or active ingredient required to be administered depend on the judgment of the practitioner. However, suitable dosage ranges for cellular vaccines are on the order of a few thousand cells to millions of cells. For standard epitope or epitope delivery vaccines, the vaccine may comprise several hundred micrograms or less of antigenic peptide per vaccination. Suitable regimes for initial administration and booster shots are also variable, but are typified by an initial administration followed by subsequent inoculations. Although the route of administration may vary, the route of delivery may be oral, intravenous, subcutaneous, peritoneal, or intramuscular.

In many instances, it will be desirable to have multiple administrations of the vaccine, e.g., four to six vaccinations provided weekly or every other week. A normal vaccination regimen will often occur in two to twelve week intervals or from three to six week intervals. Periodic boosters at intervals of 1-5 years, usually three years, may be desirable to maintain protective levels of the immune response or upon a likelihood of a remission or re-infection.

As discussed below, in certain embodiments a DDD peptide may be co-administered as an adjuvant to increase immune response to a foreign antigen, such as T20. The DDD may be separately administered, or more preferably provided in the form of a fusion protein, for example fused to T20.

T20 Gene Therapy

In gene therapy, the aim is to change the behaviour of a cell by introduction of genetic material, often DNA encoding a protein or a therapeutic RNA. Gene therapy has been used in 2142 clinical trials, with cancer diseases being the most common target (Vectors used in Gene Therapy. Gene therapy Clinical Trials Worldwide 2015). There are to date two commercially available approved gene therapy drugs—Gendicine containing a tumor suppressor gene for treatment of head and neck squamous cell carcinoma was approved in China in 2003, and Glybera targeting a lipoprotein lipase deficiency was approved in Europe in 2012 (see, e.g., Patil et al., 2005 AAPS J 8:E61-77; Ferreira et al., 2014, Front Immunol 5:82).

In order to alter cell behaviour, the genetic material must be transported into the cell and reach the nucleus. The two main ways to achieve this is either using viral vectors, where engineered viruses carry the therapeutic DNA, or nonviral vectors, which are commonly based on plasmids produced in bacteria.

Viruses have evolved specifically to deliver their genome to a target cell; this is how a virus propagates. By changing the sequence of the genetic material transported by the virus, and altering the virus to prevent it from being replication competent, this trait can be harnessed for gene therapy. Viral vectors are very efficient at delivering their cargo and have therefore been used in nearly 70% of gene therapy clinical trials (e.g., Edelstein et al., 2007, J Gene Med 9:833-42). However, there are safety issues using viral vectors (Edelstein et al., 2007, J Gene Med 9:833-42). As they originate from human pathogens, they can elicit an immune response, either because the patient has already encountered a native strain of the virus and thus carries antibodies to the vector or because repeated treatments are needed to sustain the expression of the therapeutic gene. This is the case for adenovirus and AAV derived vectors, where the transgene exists as an episome in the cell and will be diluted with cell division (Edelstein et al., 2007, J Gene Med 9:833-42).

Other viruses, such as retroviruses, integrate their genome into the genome of the target cell, and these can be engineered to do the same with a therapeutic sequence. This enables a constant expression in the cell and all daughter cells without the need for re-administration of the vector. However, the integration event can cause mutations which can have adverse effects (Edelstein et al., 2007, J Gene Med 9:833-42). In the treatment of X-linked severe combined immune deficiency using a retroviral vector, the integration caused oncogenes to be activated and five of the total 20 patients in the clinical trials suffered from leukaemia (Hacein-Bey-Abina, 2003, Science 302:415-19; Hacein-Bey-Abina, 2008, J Clin Invest 118:3132-42; Howe et al. 2008, J Clin Invest 118:3143-50). Another limitation for viral vectors is the size; there is a physical limit to the amount of genetic material that can be transported in the viral capsid.

Nonviral vectors are generally considered safer and more easily produced than viral vectors, but are less efficient in delivery and long term expression. This is thought to be partly due to the plasmid backbone, i.e. sequences needed only for propagation in the bacteria such as origin of replication and selection markers, commonly antibiotic resistance genes (Vandermeulen et al., 2011, Mol Ther 19:1942-49). Bacterially produced DNA sequences have a different methylation pattern than eukaryotic DNA. It has been shown that this can induce an immune response, especially in combination with the use of lipids for transfection (see, e.g., Bessis et al., 2004, Gene Ther 11:S10-17). Also for naked delivery of plasmids, as naked DNA lacks active transport systems for delivery into the cell and transfer into the nucleus, a nonviral vector is far less efficient than a viral vector and the expression is low and transient, which could be due in part to epigenetic phenomena.

There are many different approaches to improve the efficiency of these vectors. The plasmid can be packed together with lipids and polymers, which condense the DNA and protect it from degradation as well as facilitates uptake through fusion with the lipid bi-layer of the cell membrane (e.g., Dincer et al., 2005, Gene Therapy 12:S139-45). Another chemical method to increase transport across the cell- and nuclear membranes is to link the plasmid construct with cell penetrating peptides or nuclear ligand sequences (e.g., Jarver & Langel, 2004, Drug Discovery Today 9:395-402). Physical delivery methods use different forces to enhance transport into the target cell, such as electroporation, pneumatics or high volume infusions (Kamimura et al., 2011, Pharm Med 25:293-306).

A way to optimize the plasmid vector is to remove the bacterial backbone by recombination in the production bacteria. The resulting vector is called a minicircle (MC) (see, e.g., Nehlsen et al., 2006, Gene Ther Mol Biol 10:233-44). The smaller size of the MC, compared to plasmid or viral vectors, enables a higher dose, prolonged expression and increased robustness. The fact that the MC construct is devoid of bacterial sequences and antibiotics resistance gene make the MC vector an attractive alternative for nonviral gene therapy. In the following working Examples, a T20-expressing MC construct is provided.

T20 Minicircle Vector

Various embodiments of the present invention concern T20 expression vectors in the form of minicircle constructs. Several minicircle producing systems have been published. The first was based on the lambda phage integrase for recombination of the parental plasmid (Darquet et al., 1997, Gene Ther 4:1341-49). A later system was developed by Bigger et al. (2001, J Biol Chem 276:23018-27) and utilizes a Cre recombinase expression system with LoxP sites flanking the expression cassette. However, the loxP-sites are still active after recombination and the minicircle can be lost by the cassette recombining back into the parental plasmid again and the sites had to be mutated to ensure unidirectionality. Mayrhofer et al. (2008, J Gene Med 10:1253-69) disclosed a system based on the ParA resolvase, adding bacterial lactose operator sites in the MC construct and using affinity chromatography to purify the vector. In all these systems, the parental plasmid and the miniplasmid remain in the bacteria after recombination, and since they contain the origin of replication it is possible that they will continue to amplify in the bacteria, diluting the minicircle.

The system used in the Examples below was developed by Chen et al. (2003, Mol Ther 8:495-500; 2005, Hum Gene Ther 16:126-31) where the *Streptomyces* template integrase ΦC3 is used for recombination and the expression cassette is flanked by the attB and attP recombination sites. The resulting attR and attL sites, respectively in the minicircle and miniplasmid, cannot recombine again to reform the parental plasmid. Difficulties with separating the MC from the undesired products—the miniplasmid and any unrecombined parental plasmid—are resolved by introducing a rare restriction enzyme recognition site in the plasmid backbone outside the recombination sites, as well as providing the gene for the restriction enzyme. In the initial studies disclosed below, we used the earlier version of this system where the genes for the integrase and the restriction enzyme are encoded by the parental plasmid. Both genes were placed under the control of an arabinose inducible promoter. This approach resulted in a huge parental plasmid, but the upside was that any recombination competent *Escherichia coli* (*E. coli*) production strain could be used. However, most bacteria have an all-or-none arabinose import, where the level of arabinose inside the bacteria needs to reach a threshold level before active import is induced (Siegele et al., 1997, Proc Natl Acad Sci USA 94:8168-72). This results in a sub-population of bacteria which never reaches this threshold, where neither recombination nor digestion is induced, resulting in contamination of the desired minicircle produce with undesired plasmids. The parental plasmid and the miniplasmid contain the origin of replication, so any copies that escape degradation can continue to replicate.

The ΦC31-system was later refined by moving the genes from the parental plasmid to the bacterial genome of a bacteria strain with a constitutively active arabinose transport (Kay et al., 2010, Nat Biotechnol 28:1287-89). This results in a smaller and more stable parental plasmid and purer minicircle fraction. This system was utilized in the later studies shown below.

It has been shown that the efficiency of electroporation correlates with the size of the plasmid DNA construct (Molnar et al., 2004, Mol Ther 10:447-55), and there is a benefit of lower size also for lipofection in vitro (Kreiss et al., 1999, Nucleic Acids Res 27:3792-98) and in vivo (Loisel et al., 2001, J Liposome Res 11:127-138). Kreiss et al. (1999) discussed that the size of the pDNA may affect either the mechanism of DNA release from lipoplexes or the intracellullar migration of DNA through the cytoplasm into the nucleus, or both. McLenachan et al. (2007, Genomics 89:708-20) studied delivery of plasmid DNA ranging from five to 200 kilobasepairs (kbp) to mouse embryonic stem cells and reported a size dependant increase of nuclear delivery when using smaller constructs.

Fogg et al. (2006, J Phys Condens Matter 18:S145-59) studied recombination of MC ranging from 250 to 1000 bp. At the smaller sizes, they reported that the MC tended to form concatameric constructs rather than a monomer, and proposed that this was due to intermolecular rather than intramolecular recombination events. Their observation, of a clear inverse relationship between sequence length and efficiency of intramolecular recombination, is in accordance with our observations.

Certain embodiments involve gene therapy by administration of T20 MC to patients, to allow in vivo production and secretion of T20 peptide. To make the body produce its own protein-based drugs is an appealing thought. Yi et al. (2014, Sci Rep 4:5961) have investigated this possibility using an MC with the nucleotide sequence of etanercept and tocilizumab, two protein-based drugs for rheumatoid arthritis. They reported that these self-produced drugs were functionally active after intravenous injections of the MC in an arthritic mice model. Another study evaluated the MC in a diabetic animal model. Alam et al. (2013, PLoS One 8:e67515) used an MC construct for glucose-regulated expression of insulin delivered to the liver in diabetic rats. They reported normalized weight gain and that the treatment restored various diabetes-associated markers of metabolic dysregulation. An MC construct was also used by Park et al. (2006, J Control Release 114:118-25) to treat insulin resistance in obese mice by delivering the gene for adiponectin.

The MC form has been delivered orally, formulated as chitosan nanoparticles, to induce the expression of a modified factor IX in the small intestine in haemophilia B mice (Quade-Lyssy et al., 2014, JTH 12:932-42). Transient local transgene expression, clinically relevant levels of factor IX activity and partial phenotype correction were achieved by oral gene therapy without evidence of adverse immunological responses upon repeated administration (Quade-Lyssy et al., 2014, JTH 12:932-42).

Hyun et al. (2013, Stem Cells Transl Med 2:690-702) used an MC vector to promote stem cell survival through expression of Bcl-2, a prosurvival protein that regulates the mitochondrial pathway of apoptosis. When treating stem cells with the MC, and then delivering the transfected cells to a wound, the prosurvival protein was overexpressed and bone formation was enhanced (Hyun et al. 2013, Stem Cells Transl Med 2:690-702). There is also a study showing the suitability of the MC for transfecting stem cells and thus transgenically modify them while retaining their ability to later differentiate, suggesting that the MC might be a suitable vector for stem cell therapies when a transient expression is enough to stimulate regeneration of a tissue (Madeira et al., 2013, Biomacromolecules 14:1379-87).

A field where the MC vector has been frequently used is cancer research. Tumours have an enhanced permeability and retention, which allows both entry and sequestering of macromolecules, such as lipids, inside the tumour. Chang et al. (2014, BioMed Res Intl 2014: 156356) exploited this property to deliver a lipoplexed MC vector to Hepatitis B virus induced hepatocellular carcinoma in mice. The MC encoded a metastasis-suppressing androgen receptor, and the transgenic protein could be detected for up to 60 days (Chang et al., 2014, BioMed Res Intl 2014: 156356). Wu et al. (2006, Clin Cancer Res 12:4702-13) studied expression of tumour necrosis factor alpha from MC vectors in vitro and in vivo into xenografts of nasopharyngeal carcinoma in mice, and show good expression in vitro and reduction of xenograft tumour growth and prolonged survival in vivo, although the MC only outperformed the large parental plasmid in vivo when using the same weight dose (Wu et al., 2006, Clin Cancer Res 12:4702-13). They showed expression in tumours for 21 days after treatment from MC, declining over time, whereas the expression from the large parental plasmid was all but lost after seven days (Wu et al., 2006, Clin Cancer Res 12:4702-13). The same group later constructed an MC encoding endostatin, an angiogenesis inhibitor, and evaluated it in the same xenograft model of nasopharyngeal carcinoma (Xu et al., 2012, Cancer Gene Ther 19:110-17). They reported reduced tumour growth for the full 20 days of the experiment as well as reduced vascularisation of the tumour after intratumoural injections (Xu et al., 2012, Cancer Gene Ther 19:110-17).

In an interesting cancer therapy study, Gaspar et al. (2014, J Control Release 189:90-104) used micelle nanocarriers to co-deliver an MC encoding the tumour necrosis factor alpha related apoptosis-inducing ligand and a chemotherapeutic drug, doxorubicin. They observed good uptake in vitro and an anti-tumoural effect in mice at relatively low concentrations (Gaspar et al., 2014, J Control Release 189:90-104).

miMCs encoding shRNAs have been used in muscle, and also as expression vectors for inhibitory agents preventing viral replication. In a study by Yang et al. (2012, Antiviral Res 96:234-44), two viruses that are major causative agents of hand, foot and mouth disease were targeted. Expression of the shRNAs from the miMC vector blocked the replication and gene expression of these viruses in vitro and in a virus-infected mouse model, with an alleviation of symptoms in the infected mice (Yang et al., 2012, Antiviral Res 96:234-44). In this study, Yang et al. designed a system for expression of two shRNAs from the same coding sequences, by flanking the sequence with two different promoters in different directions, as an snRNA is symmetric in sense and antisense.

A special case of a protein expressing vector is a plasmid designed for DNA vaccination. Among the advantages of using plasmids are the ease of both development and production as compared with conventional vaccine manufacturing. Moreover, DNA vaccines are known to be very stable at room temperature, which is of significance for both transport and storage (Quaak et al., 2010, AAPS PharmSciTech 11:344-50). Since the antigen is expressed from pDNA within the target cell, the resulting peptide is more likely to resemble the native form, of e.g. a viral protein, with all the necessary post-translational modifications.

In a report by Dietz et al. (2013, Mol Ther 21:1526-35), an MC construct showed promise as a DNA vaccine vector. The MC had a higher and more prolonged expression in vitro and in vivo in mice and an enhanced immunogenicity in vivo. In a challenge experiment, the MC vector conferred better protection and elicited a stronger antigen specific CD8+ T-cell response in a mouse model of listeriosis (Dietz et al., 2013, Mol Ther 21:1526-35). CD8+ T-cells are an important component of the cellular immune response against any viral infection as they can recognize and eliminate infected cells. Thus, a strong CD8+ T-cell response could be of significance for HIV vaccination. HIV mainly targets CD4+ T-cells and by thus affecting the function of these cells, HIV impairs the maturation of CD8+ T-cell Gulzar & Copeland, 2004, Current HIV Res 2:23-37).

Wang et al. (2014, J Virol 88:1924-34) used an MC expressing an HIV protein for vaccination purposes. In their experiments, the humoral and cellular immune response when using an MC was twice that of a conventional plasmid. Notably, in their study they also saw that intramuscular injection of an MC with in vivo electroporation induced the strongest humoral and cellular immune responses as compared to intramuscular injections alone, intradermal injections with or without electroporation, or high volume perfusion of the liver (Wang et al., 2014, J Virol 88:1924-34). Wang et al. also reported that the improvement of expression when using electroporation was four times higher for an MC vector than for a conventional plasmid.

These and other known methods and compositions for use of therapeutic minicircles may be used in the practice of the claimed invention.

Combination Therapy

As discussed above, therapy with T20 peptide and/or minicircle may be enhanced by combination with other anti-viral agents. Numerous such agents are known in the art, including but not limited to abacavir, amdoxovir, apricitabine, atazanavir, bevirimat, calanolide A, CCR5, CD4, ceragenin, cobicistat, cyanovirin-N, darunavir, diarylpyrimidines, didanosine, dolutegravir, efavirenz, elvitegravir, elvucitabine, emtricitabine, epigallotachen gallate, festinavir, fosamprenavir, foscarnet, griffithsin, globoidnan A, hydroxycarbamide, indinavir, KP-146, lamivudine, lefinavir, lersivirine, lopinavir, miltefosine, MK-2048, nelfinavir, nevirapine, racivir, raltegravir, ritonavir, saquinavir, selicicib, stafudine, stampidine, stavudine, Tat antagonists, tenofovir, tipranavir, trichosanthin, TRIM5alpha, vivecon, zalcitabine, zidovudine or zidovudine.

One type of anti-HIV agent comprises neutralizing antibodies or fragments thereof that are capable of destroying or inhibiting the infectivity and/or virulence of HIV. A variety of HIV neutralizing antibodies are known in the art and any such known antibodies or fragments thereof may be used, including but not limited to P4/D10, 2G12 (e.g., Joos et al., *Antimicrob Agents Chemother* 2006, 50:1773-79), 4E10 (Joos et al., 2006), 2F5 (Joos et al., 2006), b12 (e.g., Wu et al., *J Virol* 2006, 80:2585), X5 (Moulard et al., *Proc Natl Acad Sci* 2002, 99:6913-18) or any combination thereof. Where multispecific antibodies or fragments are used, or combinations of monospecific antibodies, the skilled artisan will realize that multiple antibodies or fragments that bind to the same or different HIV epitopes may be combined. Although antibodies against the HIV envelope protein (gp120) and/or gp41 are preferred, the skilled artisan will realize that other HIV target antigens may be utilized to develop antibodies or fragments thereof that will target HIV-infected cells. In some cases, antibodies or fragments that bind to one or more HIV antigens in combination with T-cell antigens (e.g., CD4, CCR5 and/or CXCR4) may be utilized.

Another class of potential therapeutic agents consists of aggresome inhibitors. Aggresomes are large intracellular complexes that were thought to form in response to misfolded protein (see, e.g., Heath et al., J. Cell Biol. 153:449-55, 2001; Johnstone et al., J. Cell Biol. 143:1883-98, 1998; Wileman, Science 312:875-78, 2006). More recently, it has been suggested that aggresomes may function in the assembly of viral particles (Heath et al., 2001; Wileman, 2006). Aggresome inhibitors may therefore function to block or inhibit the formation of new infectious viral particles from cells infected with HIV or other viruses. A variety of aggresome inhibitors are known, such as ALLN, nocodazole, colchicine and vinblastine (Johnston et al., 1998), other microtubule inhibitors (Gerdes and Katsanis, Hum. Molec. Genet. 14:R291-300, 2005); bortezomib (Catley et al., Blood 108:3441-49, 2006), tubacin, histone deacetylase inhibitors (Corcoran et al., Curr. Biol. 14:488-92, 2004), and any such known aggresome inhibitor may be used.

In various embodiments, one or more immunomodulators may be used. As used herein, the term "immunomodulator" includes cytokines, stem cell growth factors, lymphotoxins and hematopoietic factors, such as interleukins, colony stimulating factors, interferons (e.g., interferons-α, -β and -γ) and the stem cell growth factor designated "S1 factor."

Examples of suitable immunomodulator moieties include IL-2, IL-6, IL-10, IL-12, IL-18, IL-21, interferon-gamma, TNF-alpha, and the like.

The term "cytokine" is a generic term for proteins or peptides released by one cell population which act on another cell as intercellular mediators. As used broadly herein, examples of cytokines include lymphokines, monokines, growth factors and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-10, IL-11, IL-12; IL-13, IL-14, IL-15, IL-16, IL-17, IL-18, IL-21, LIF, G-CSF, GM-CSF, M-CSF, EPO, kit-ligand or FLT-3, angiostatin, thrombospondin, endostatin, tumor necrosis factor and LT. As used herein, the term cytokine includes proteins from natural sources or from recombinant cell culture and biologically active equivalents of the native sequence cytokines.

Chemokines generally act as chemoattractants to recruit immune effector cells to the site of chemokine expression. It may be advantageous to express a particular chemokine gene in combination with, for example, a cytokine gene, to enhance the recruitment of other immune system components to a site of treatment. Chemokines include, but are not limited to, RANTES, MCAF, MIP1-alpha, MIP1-Beta, and IP-10. The skilled artisan will recognize that certain cytokines are also known to have chemoattractant effects and could also be classified under the term chemokines. Similarly, the terms immunomodulator and cytokine overlap in their respective members.

The T20 fusion inhibitor could potentially be used in combination with a different fusion inhibitor. HIV fusion inhibitors are described in PCT Patent Application Publ. No. WO 2007045463. It is known that the amino acid sequence of the gp41 protein differs between the different HIV strains because of naturally occurring polymorphisms. But the same domain architecture can be recognized, a fusion signal, two heptad repeat domains (HR1, HR2) and a transmembrane domain. The fusion (or fusogenic) domain participates in the insertion into and disintegration of the cell membrane. Peptides with amino acid sequences deduced from the HR1 or HR2 domain of gp41 are effective in vitro and in vivo inhibitors of HIV uptake into cells (see, e.g. U.S. Pat. Nos. 5,464,933; 5,656,480; 6,258,782; 6,348,568; 6,656,906). For example, T20, an HR2 peptide and T651 (U.S. Pat. No. 6,479,055) are potent inhibitors of HIV infection. Attempts have been made to enhance the efficacy of HR2 derived peptides, for example by amino acid substitution or chemical crosslinking (Sia et al, 2002, PNAS USA 99:14664-14669; Otaka et al, 2002, Angew. Chem. Int. 41:2937-2940).

Exemplary anti-fusogenic peptides are found in U.S. Pat. Nos. 5,464,933; 5,656,480; 6,013,263; 6,017,536; 6,020,459; 6,093,794; 6,060,065; 6,258,782; 6,348,568; 6,479,055; 6,656,906; and PCT Patent Application Publ. Nos. WO 1996/19495, WO 1996/40191, WO 1999/59615, WO 2000/69902, and WO 2005/067960, the Examples section of each incorporated herein by reference.

In certain embodiments a minicircle or other vector may be utilized to deliver an siRNA or interference RNA species. A variety of carrier moieties for siRNA have been reported and any such known carrier may be used. Non-limiting examples of carriers include protamine (Rossi, 2005, Nat Biotech 23:682-84; Song et al., 2005, Nat Biotech 23:709-17); dendrimers such as PAMAM dendrimers (Pan et al., 2007, Cancer Res. 67:8156-8163); polyethylenimine (Schiffelers et al., 2004, Nucl Acids Res 32:e149); polypropyleneimine (Taratula et al., 2009, J Control Release 140:284-93); polylysine (Inoue et al., 2008, J Control Release 126:59-66); histidine-containing reducible polycations (Stevenson et al., 2008, J Control Release 130:46-56); histone H1 protein (Haberland et al., 2009, Mol Biol Rep 26:1083-93); cationic comb-type copolymers (Sato et al., 2007, J Control Release 122:209-16); polymeric micelles (U.S. Patent Application Publ. No. 20100121043); and chitosan-thiamine pyrophosphate (Rojanarata et al., 2008, Pharm Res 25:2807-14). The skilled artisan will realize that in general, polycationic proteins or polymers are of use as siRNA carriers. The skilled artisan will further realize that siRNA carriers can also be used to carry other oligonucleotide or nucleic acid species, such as anti-sense oligonucleotides or short DNA genes.

Many siRNA species are commercially available from known sources, such as Sigma-Aldrich (St Louis, Mo.), Invitrogen (Carlsbad, Calif.), Santa Cruz Biotechnology (Santa Cruz, Calif.), Ambion (Austin, Tex.), Dharmacon (Thermo Scientific, Lafayette, Colo.), Promega (Madison, Wis.), Minis Bio (Madison, Wis.) and Qiagen (Valencia, Calif.), among many others. Other publicly available sources of siRNA species include the siRNAdb database at the Stockholm Bioinformatics Centre, the MIT/ICBP siRNA Database, the RNAi Consortium shRNA Library at the Broad Institute, and the Probe database at NCBI. For example, there are 30,852 siRNA species in the NCBI Probe database. The skilled artisan will realize that for any gene of interest, either a siRNA species has already been designed, or one may readily be designed using publicly available software tools.

Dock-and-Lock® (DNL®)

In certain embodiments, antigenic fusion proteins or complexes may be formed by the DOCK-AND-LOCK® (DNL®) technology (see, e.g., U.S. Pat. Nos. 7,521,056; 7,527,787; 7,534,866; 7,550,143 and 7,666,400, the Examples section of each of which is incorporated herein by reference.) Generally, the technique takes advantage of the specific and high-affinity binding interactions that occur between a dimerization and docking domain (DDD) sequence of the regulatory (R) subunits of cAMP-dependent protein kinase (PKA) and an anchor domain (AD) sequence derived from any of a variety of AKAP proteins (Baillie et al., FEBS Letters. 2005; 579: 3264. Wong and Scott, Nat. Rev. Mol. Cell Biol. 2004; 5: 959). The DDD and AD peptides may be attached to any protein, peptide or other molecule. Because the DDD sequences spontaneously dimerize and bind to the AD sequence, the technique allows the formation of complexes between any selected molecules that may be attached to DDD or AD sequences. Although the standard DNL® complex comprises a trimer with two DDD-linked molecules attached to one AD-linked molecule, variations in complex structure allow the formation of dimers, trimers, tetramers, pentamers, hexamers and other multimers. The DNL® complex or fusion protein may comprise one or more other effectors, such as proteins, peptides, antibodies, antibody fragments, immunomodulators, cytokines, interleukins, interferons, binding proteins, peptide ligands, carrier proteins, toxins, ribonucleases such as onconase, inhibitory oligonucleotides such as siRNA, antigens or xenoantigens, polymers such as PEG, enzymes, therapeutic agents, hormones, cytotoxic agents, anti-angiogenic agents, pro-apoptotic agents or any other molecule or aggregate.

PKA, which plays a central role in one of the best studied signal transduction pathways triggered by the binding of the second messenger cAMP to the R subunits, was first isolated from rabbit skeletal muscle in 1968 (Walsh et al., J. Biol. Chem. 1968; 243:3763). The structure of the holoenzyme consists of two catalytic subunits held in an inactive form by the R subunits (Taylor, J. Biol. Chem. 1989; 264:8443). Isozymes of PKA are found with two types of R subunits (RI and RII), and each type has α and β isoforms (Scott, Pharmacol. Ther. 1991; 50:123). Thus, the four isoforms of PKA regulatory subunits are RIα, RIβ, RIIα and RIIβ. The R subunits have been isolated only as stable dimers and the dimerization domain has been shown to consist of the first 44 amino-terminal residues of RIIα (Newlon et al., Nat. Struct. Biol. 1999; 6:222). As discussed below, similar portions of the amino acid sequences of other regulatory subunits are involved in dimerization and docking, each located near the N-terminal end of the regulatory subunit. Binding of cAMP to the R subunits leads to the release of active catalytic subunits for a broad spectrum of serine/threonine kinase activities, which are oriented toward selected substrates through the compartmentalization of PKA via its docking with AKAPs (Scott et al., J. Biol. Chem. 1990; 265; 21561)

Since the first AKAP, microtubule-associated protein-2, was characterized in 1984 (Lohmann et al., Proc. Natl. Acad. Sci USA. 1984; 81:6723), more than 50 AKAPs that localize to various sub-cellular sites, including plasma membrane, actin cytoskeleton, nucleus, mitochondria, and endoplasmic reticulum, have been identified with diverse structures in species ranging from yeast to humans (Wong and Scott, Nat. Rev. Mol. Cell Biol. 2004; 5:959). The AD of AKAPs for PKA is an amphipathic helix of 14-18 residues (Carr et al., J. Biol. Chem. 1991; 266:14188). The amino acid sequences of the AD vary among individual AKAPs, with the binding affinities reported for RII dimers ranging from 2 to 90 nM (Alto et al., Proc. Natl. Acad. Sci. USA. 2003; 100:4445). AKAPs will only bind to dimeric R subunits. For human RIIα, the AD binds to a hydrophobic surface formed by the 23 amino-terminal residues (Colledge and Scott, Trends Cell Biol. 1999; 6:216). Thus, the dimerization domain and AKAP binding domain of human RIIα are both located within the same N-terminal 44 amino acid sequence (Newlon et al., Nat. Struct. Biol. 1999; 6:222; Newlon et al., EMBO J. 2001; 20:1651), which is termed the DDD herein.

We have developed a platform technology to utilize the DDD of human PKA regulatory subunits and the AD of AKAP as an excellent pair of linker modules for docking any two entities, referred to hereafter as A and B, into a noncovalent complex, which could be further locked into a DNL® complex through the introduction of cysteine residues into both the DDD and AD at strategic positions to facilitate the formation of disulfide bonds. The general methodology of the approach is as follows. Entity A is constructed by linking a DDD sequence to a precursor of A, resulting in a first component hereafter referred to as a. Because the DDD sequence would effect the spontaneous formation of a dimer, A would thus be composed of $a_2$. Entity B is constructed by linking an AD sequence to a precursor of B, resulting in a second component hereafter referred to as b. The dimeric motif of DDD contained in $a_2$ will create a docking site for binding to the AD sequence contained in b, thus facilitating a ready association of $a_2$ and b to form a binary, trimeric complex composed of $a_2b$. This binding event is made irreversible with a subsequent reaction to covalently secure the two entities via disulfide bridges, which occurs very efficiently based on the principle of effective local concentration because the initial binding interactions should bring the reactive thiol groups placed onto both the DDD and AD into proximity (Chmura et al., Proc. Natl. Acad. Sci. USA. 2001; 98:8480) to ligate site-specifically. Using various combinations of linkers, adaptor modules and precursors, a wide variety of DNL® constructs of different stoichiometry may be produced and used (see, e.g., U.S. Pat. Nos. 7,550,143; 7,521,056; 7,534,866; 7,527,787 and 7,666,400.)

By attaching the DDD and AD away from the functional groups of the two precursors, such site-specific ligations are also expected to preserve the original activities of the two precursors. This approach is modular in nature and potentially can be applied to link, site-specifically and covalently, a wide range of substances, including peptides, proteins, antibodies, antibody fragments, and other effector moieties with a wide range of activities. Utilizing the fusion protein method of constructing AD and DDD conjugated effectors described in the Examples below, virtually any protein or peptide may be incorporated into a DNL® construct. However, the technique is not limiting and other methods of conjugation may be utilized.

A variety of methods are known for making fusion proteins, including nucleic acid synthesis, hybridization and/or amplification to produce a synthetic double-stranded nucleic acid encoding a fusion protein of interest. Such double-stranded nucleic acids may be inserted into expression vectors for fusion protein production by standard molecular biology techniques (see, e.g. Sambrook et al., Molecular Cloning, A laboratory manual, $2^{nd}$ Ed, 1989). In such preferred embodiments, the AD and/or DDD moiety may be attached to either the N-terminal or C-terminal end of an effector protein or peptide. However, the skilled artisan will realize that the site of attachment of an AD or DDD moiety to an effector moiety may vary, depending on the chemical nature of the effector moiety and the part(s) of the effector moiety involved in its physiological activity. Site-specific attachment of a variety of effector moieties may be performed using techniques known in the art, such as the use of bivalent cross-linking reagents and/or other chemical conjugation techniques.

In certain embodiments, discussed in more detail in the Examples below, a DDD moiety may be incorporated in a fusion protein with another antigenic peptide or protein, in order to induce a stronger immune response against the target antigen. In a specific embodiment, an exemplary fusion protein comprises a DDD2 moiety attached via a linker to a T20 peptide. Because the T20 sequence mimics part of the gp41 protein of HIV, introduction of the fusion protein, or expression vectors that can produce the fusion protein, into a host can induce an immune response that can protect against HIV infection, or can suppress an existing HIV infection. As discussed below, other DDD moieties are known and may be utilized for construction of antigenic fusion proteins. The person of ordinary skill will realize that the target antigen used in combination with a DDD moiety to induce immune response is not limited to T20. Other target antigens known in the art, for therapy of diseases such as cancer, autoimmune disease or pathogen infection, may also be incorporated in the subject fusion proteins along with a DDD moiety.

Structure-Function Relationships in AD and DDD Moieties

For different types of DNL® constructs, different AD or DDD sequences may be utilized. Exemplary DDD and AD sequences are provided below.

```
DDD1
                                            (SEQ ID NO: 4)
SHIQIPPGLTELLQGYTVEVLRQQPPDLVEFAVEYFTRLREARA

DDD2
                                            (SEQ ID NO: 5)
CGHIQIPPGLTELLQGYTVEVLRQQPPDLVEFAVEYFTRLREARA

AD1
                                            (SEQ ID NO: 6)
QIEYLAKQIVDNAIQQA

AD2
                                            (SEQ ID NO: 7)
CGQIEYLAKQIVDNAIQQAGC
```

The skilled artisan will realize that DDD1 and DDD2 are based on the DDD sequence of the human RIIα isoform of protein kinase A. However, in alternative embodiments, the DDD and AD moieties may be based on the DDD sequence of the human Ma form of protein kinase A and a corresponding AKAP sequence, as exemplified in DDD3, DDD3C and AD3 below.

```
DDD3
                                            (SEQ ID NO: 8)
SLRECELYVQKHNIQALLKDSIVQLCTARPERPMAFLREYFERLEK
EEAK

DDD3C
                                            (SEQ ID NO: 9)
MSCGGSLRECELYVQKHNIQALLKDSIVQLCTARPERPMAFLREYF
ERLEKEEAK

AD3
                                            (SEQ ID NO: 10)
CGFEELAWKIAKMIWSDVFQQGC
```

In other alternative embodiments, other sequence variants of AD and/or DDD moieties may be utilized in construction of the DNL® complexes. For example, there are only four variants of human PKA DDD sequences, corresponding to the DDD moieties of PKA RIα, RIIα, RIβ and RIIβ. The RIIα DDD sequence is the basis of DDD1 and DDD2 disclosed above. The four human PKA DDD sequences are shown below. The DDD sequence represents residues 1-44 of RIIα, 1-44 of RIIβ, 12-61 of RIα and 13-66 of RIβ. (Note that the sequence of DDD1 is modified slightly from the human PKA RIIα DDD moiety.) Any of the disclosed DDD sequences, or other known DDD sequences, may be utilized to construct a fusion protein or alternative construct with enhanced antigenic activity.

PKA RIα

(SEQ ID NO: 11)
SLRECELYVQKHNIQALLKDVSIVQLCTARPERPMAFLREYFEKLE
KEEAK

PKA RIβ

(SEQ ID NO: 12)
SLKGCELYVQLHGIQQVLKDCIVHLCISKPERPMKFLREHFEKLEK
EENRQILA

PKA RIIα

(SEQ ID NO: 13)
SHIQIPPGLTELLQGYTVEVGQQPPDLVDFAVEYFTRLREARRQ

PKA RIIβ

(SEQ ID NO: 14)
SIEIPAGLTELLQGFTVEVLRHQPADLLEFALQHFTRLQQENER

Formulation and Administration

The anti-HIV therapeutic agents disclosed herein may be further formulated to obtain compositions that include one or more pharmaceutically suitable excipients, one or more additional ingredients, or some combination of these. These can be accomplished by known methods to prepare pharmaceutically useful dosages, whereby the active ingredients are combined in a mixture with one or more pharmaceutically suitable excipients. Sterile phosphate-buffered saline is one example of a pharmaceutically suitable excipient. Other suitable excipients are well known to those in the art. See, e.g., Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

One route for administration of the compositions described herein is parenteral injection. In parenteral administration, the compositions will be formulated in a unit dosage injectable form such as a solution, suspension or emulsion, in association with a pharmaceutically acceptable excipient. Such excipients are inherently nontoxic and non-therapeutic. Examples of such excipients are saline, Ringer's solution, dextrose solution and Hank's solution. Nonaqueous excipients such as fixed oils and ethyl oleate may also be used. The excipient may contain minor amounts of additives such as substances that enhance isotonicity and chemical stability, including buffers and preservatives.

Formulated compositions can be used for intravenous administration via, for example, bolus injection or continuous infusion. Other methods of administration include subcutaneous, intramuscular, intravascular or localized infusion or by oral delivery. Compositions for administration can be presented in unit dosage form, e.g., in ampules or in multi-dose containers, with an added preservative. Compositions can also take such forms as suspensions, solutions or emulsions in oily or aqueous vehicles, and can contain formulatory agents such as suspending, stabilizing and/or dispersing agents. Alternatively, the compositions can be in powder form for constitution with a suitable vehicle, e.g., sterile pyrogen-free water, before use.

The compositions may be administered in solution. The formulation thereof should be in a solution having a suitable pharmaceutically acceptable buffer such as phosphate, tris (hydroxymethyl) aminomethane-HCl or citrate and the like. Buffer concentrations should be in the range of 1 to 100 mM. The formulated solution may also contain a salt, such as sodium chloride or potassium chloride in a concentration of 50 to 150 mM. An effective amount of a stabilizing agent such as glycerol, albumin, a globulin, a detergent, a gelatin, a protamine or a salt of protamine may also be included.

Kits

Some embodiments concern kits for practicing the claimed methods. The kit may include a T20 minicircle or expressed peptide. The kit components may be packaged into containers, such as vials that contain sterile, lyophilized formulations of a composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers. Another component that can be included is instructions to a person using a kit for its use.

EXAMPLES

The following examples are included to demonstrate preferred embodiments of the invention. It should be appreciated by those of skill in the art that the techniques disclosed in the Examples which follow represent techniques discovered to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1. General Methods and Compositions Relating to T20 MCs

MC Vector Production

Initially, the expression cassette containing a CMV promoter, the gene for hVEGF-165 and a rabbit β-globin polyadenylation site was cloned from the phVEGF 165-vector into the p2ΦC31 MC producing plasmid between the two recombination sites. This was the first generation of the ΦC3 MC producing system developed by Chen et al. (2003, Mol Ther 8:495-500; 2005, Hum Gene Ther 16:126-31). In this system, the inducible genes for the recombinase and endonuclease are located on the parental plasmid and production could be performed in any recombination competent E. coli production strain. After over-night propagation of the transduced bacteria, addition of arabinose induced the pBAD-promoter controlling the Streptomyces phage ΦC31 integrase gene and the I-Sec-I endonuclease gene. Thus, recombination of the parental plasmid into the MC and miniplasmid was induced, as well as linearization of the miniplasmid by the endonuclease at the recognition sites located outside the recombination sites. This step took place at 32° C. at increased pH to improve the efficiency of the enzymes. After five hours, the bacteria are harvested and the MC vector purified.

Later, an improved system with the specialized ZYCY10P3S2T bacterial strain was used (Kay et al., 2010, Nature Biotech 28:1287-89). The expression cassettes used were U7asLuc, with antisense sequences targeting the mutated β-globin intron (Kang et al., 1998, Biochem 37:6235-39) and U7asDys with a sequence targeting across the splicing branching point in intron 22 and the U1 binding region at the donor site in intron 23 in mdx dystrophin pre-mRNA (Goyenvalle et al., 2004, Science 306:1796-99). The modified U7 gene, along with its natural promoter and 3' elements was cloned into the pMC parental plasmid between the two recombination sites. After transduction of the ZYCY10P3S2T bacteria, carrying the inducible genes for the ΦC3 integrase and the I-Sec-I endonuclease, miMCs were produced according to the method published by Kay et al. (2010, Nature Biotech 28:1287-89).

All the MCs used were produced in small scale fermentations in a shaking incubator. In an experiment to produce MCs on a larger scale, we utilized a pilot plant scale fermentor. A fermentor is a type of bioreactor containing and controlling the culture of microorganisms, in our case bacteria. The fermentor contains a suitable growth medium and has been inoculated with a bacterial culture to start the fermentation process. It controls the temperature, pH, ventilation and agitation of the culture. It can also be set to control the conditions of nutrients by using a fed-batch system that adds buffers continuously or at set time points during the fermentation process, e.g. for induction of recombination by addition of arabinose. Fermentation allows for a much higher density of bacteria and thus a higher yield of plasmid or MC DNA.

MC DNA was purified using commercial kits from QIAGEN (Hilden, Germany) according to the manufacturer's protocol, with the modification that larger buffer volumes are needed for the lysis steps. After purification, quantity and quality were assayed using UV spectrophotometry at 260 nm and agarose gel electrophoresis.

For some uses, it is important to have only one isomer present in the final product, i.e. the monomeric T20 MC without any contaminating plasmids. We therefore performed an additional gel separation and purification of the isomer of interest. MC DNA was separated by size on an agarose gel. Care was taken to avoid nicking the DNA by UV light or intercalating dye: the isomer's position in the gel was marked on stained edges of the gel and the corresponding band excised from the unstained gel. The monomer was then extracted from this gel fragment by QIAquick Gel Extraction Kit (QIAGEN) according to the manufacturer's protocol and further purified by phenol:chloroform extraction.

Pneumatic Delivery the ability of MCs of different sizes to withstand the shearing forces induced by pneumatic delivery was evaluated by injecting the DNA vector through mouse skin using a BIOJECTOR® (Bioject Medical Technologies Inc, CA, USA). MC integrity was analyzed by gel electrophoresis.

The BIOJECTOR® is a needle free system for drug delivery by forcing liquid medications through a tiny orifice that is held against the skin. Pneumatics and the small diameter of the orifice create an ultra-fine stream of high-pressure fluid that penetrates the skin without using a needle. The BIOJECTOR® can deliver injections to various depths, with intramuscular injections being the deepest injection type. Most vaccines are currently delivered to the intramuscular depth. The BIOJECTOR® can also deliver agents subcutaneously to the adipose layer below the skin, as well as intradermally. In various methods, pneumatic delivery may be used to administer the T20 MC to human subjects.

Lipofection

FUGENE® 6 (Roche, Mannheim, Germany) was used for lipofection of MC construct into HT-1080, a human fibrosarcoma cell line, with a reagent:DNA ratio of 3:1 per the manufacturer's protocol. Cells were seeded one day prior to transfection in an appropriate density so that they are 70-80% confluent at the day of transfection. Cells were processed 48 h later.

In another study, HeLa Luc/705 cells were transfected using LIPOFECTAMINE® 2000 (ThermoScientific) according to manufacturer's protocol. Briefly, cells were seeded one day prior to transfection in an appropriate density so that they were 70-80% confluent at the day of transfection. DNA was complexed using 2.3 µl of LIPOFECTAMINE® 2000 per µg of DNA in OPTI-MEM® (ThermoScientific). Cells were processed 24 h after transfection. Lipofection is an alternative technique for delivery of T20 MC for human therapeutic use.

Electroporation

HeLa Luc/705 cells were also transfected using electroporation. Electroporation is a physical transfection method which enables direct delivery over the cell membrane and into the nucleus. Electroporation occurs when an external electric field is applied to the cell and the transmembrane potential exceeds a critical threshold (Golzio et al., 2004, Methods 33:126-35). This leads to a transient permeabilization of the plasma membrane, possibly through the creation of nanoscale pores, that allows DNA delivery into cell. We used the NEON® transfection system (ThermoScientific) in which cells are treated in suspension in a pipette tip chamber where the electric field is generated.

In Vivo Delivery

Direct injection of pDNA into muscle results in expression of the DNA in myofiber cells. Uptake and expression of numerous transgenes have been demonstrated in various species following intramuscular injections of naked DNA (Braun, 2008, Curr Gene Ther 8:391-405). The expression peaks after a few days and then drops to a lower but steady expression, and can be detected for a very long time in some cases (Wolff et al., 1992, Hum Mol Gen 1:363-69). However, the efficiency of pDNA gene transfer into skeletal muscle is low, with around one percent of the cells being transfected after an intramuscular injection (Jiao et al., 1992, Hum Gene Ther 3:21-33). Also, expression is only seen in a very restricted area of the muscle, usually along the needle track. In specific embodiments, direct injection may be utilized to administer T20 MC for therapeutic use.

Hydrodynamic Delivery

Hydrodynamic infusion is a well-documented gene transfer technique, known to give a high transfection efficiency of the liver in mice (Suda & Liu, 2007, Mol Ther 15:2063-69). By rapid injection of a relatively large volume of DNA solution, a controlled hydrodynamic pressure arises in the capillaries which enhances cell permeability and allows for entry into the hepatocytes. The discontinuous sinusoidal capillaries in liver are sensitive to the hydrodynamic procedure, and the high pressure is thought to induce membrane pores in the hepatocytes which are responsible for intracellular DNA transfer. When the pressure is reduced, the pores close and the material is trapped inside the cell (Zhang et al., 2004, Gene Ther 11:675-82; Al-Dosari et al., 2005, Adv Genetics 54:65-82).

In an exemplary process, mice were treated with a two ml hydrodynamic infusion through the tail vein while anesthetized, the volume being about 10% of the mice body weight. This provided long term expression in vivo. In some embodiments, hydrodynamic delivery may be utilized for human therapy with T20 MC.

Electroporation In Vivo

Electrotransfer in vivo is based on injection of pDNA solution into the muscle, followed by the application of a series of electric pulses over the tissue. Electroporation has been shown to increase the gene transfer not only by cell permeabilization but also by a direct active effect on the DNA molecule, promoting DNA migration and cellular uptake. Pre-treating the muscle with bovine hyaluronidase has been shown to ameliorate the cell damage associated with electroporation (Gollins et al., 2003, Gene Ther 10:504-512). This method is reported to result in a higher transduction than high pressure delivery methods, resulting in expression levels comparable to those achieved with viral vectors (Konieczny et al., 2013, Muscle & Nerve 47:649-63). Even though electroporation is a rather invasive method for gene delivery, studies have shown that it is feasible to deliver nonviral vectors in vivo using electroporation to rat diaphragm (Beshay et al., 2009, Dev Growth Differ 51:547-53).

Electroporation was performed to enhance the efficiency of intramuscular injection of MC into skeletal muscle. Hyaluronidase treatment, injection and electroporation of mdx mice was performed according to Wells et al. (2008, Methods Mol Biol 423:421-31). Electroporation may be used to administer T20 MC to subjects for therapeutic use, to improve efficiency of cell transduction.

Example 2. Production of T20 Microcircle Vector

We cloned the T20 coding sequence and an expression cassette used in HIV vaccine studies into the pMC-vector for minicircle production. The construct containing the T20 coding sequence (amino acid sequence shown in SEQ ID NO:2) was provided by Immunomedics. Following induction of recombination, the resulting MC was 1.1 kb, i.e. less than one third of a corresponding conventional plasmid. The DNA sequence of the resulting T20 MC vector is shown in SEQ ID NO:1.

```
T20 Minicircle Sequence
                                           (SEQ ID NO: 1)
ACATTACCCTGTTATCCCTAGATGACATTACCCTGTTATCCCAGATGA

CATTACCCTGTTATCCCTAGATGACATTACCCTGTTATCCCTAGATGA

CATTTACCCTGTTATCCCTAGATGACATTACCCTGTTATCCCAGATGA

CATTACCCTGTTATCCCTAGATACATTACCCTGTTATCCCAGATGACA

TACCCTGTTATCCCTAGATGACATTACCCTGTTATCCCAGATGACATT

ACCCTGTTATCCCTAGATACATTACCCTGTTATCCCAGATGACATACC

CTGTTATCCCTAGATGACATTACCCTGTTATCCCAGATGACATTACCC

TGTTATCCCTAGATACATTACCCTGTTATCCCAGATGACATACCCTGT

TATCCCTAGATGACATTACCCTGTTATCCCAGATGACATTACCCTGTT

ATCCCTAGATACATTACCCTGTTATCCCAGATGACATACCCTGTTATC

CCTAGATGACATTACCCTGTTATCCCAGATGACATTACCCTGTTATCC

CTAGATACATTACCCTGTTATCCCAGATGACATACCCTGTTATCCCTA

GATGACATTACCCTGTTATCCCAGATGACATTACCCTGTTATCCCTAG

ATACATTACCCTGTTATCCCAGATGACATACCCTGTTATCCCTAGATG

ACATTACCCTGTTATCCCAGATAAACTCAATGATGATGATGATGATGG

TCGAGACTCAGCGGCCGCGGTGCCAGGGCGTGCCCTTGGGCTCCCCGG

GCGCGACTAGTGAATTCAGATCTGATATCTCTAGAGGCCCATTGCATA

CGTTGTATCCATATCATAATATGTACATTTATATTGGCTCATGTCCAA

CATTACCGCCATGTTGACATTGATTATTGACTAGTTATTAATAGTAAT

CAATTACGGGGTCATTAGTTCATAGCCCATATATGGAGTTCCGCGTTA

CATAACTTACGGTAAATGGCCCGCCTGGCTGACCGCCCAACGACCCCC

GCCCATTGACGTCAATAATGACGTATGTTCCCATAGTAACGCCAATAG

GGACTTTCCATTGACGTCAATGGGTGGAGTATTTACGGTAAACTGCCC

ACTTGGCAGTACATCAAGTGTATCATATGCCAAGTACGCCCCCTATTG

ACGTCAATGACGGTAAATGGCCCGCCTGGCATTATGCCCAGTACATGA

CCTTATGGGACTTTCCTACTTGGCAGTACATCTACGTATTAGTCATCG

CTATTACCATGGTGATGCGGTTTTGGCAGTACATCAATGGGCGTGGAT

AGCGGTTTGACTCACGGGGATTTCCAAGTCTCCACCCCATTGACGTCA

ATGGGAGTTTGTTTTGGCACCAAAATCAACGGGACTTTCCAAAATGTC

GTAACAACTCCGCCCCATTGACGCAAATGGGCGGTAGGCGTGTACGGT

GGGAGGTCTATATAAGCAGAGCTCGTTTAGTGAACCGTCAGATCGCCT

GGAGACGCCATCCACGCTGTTTTGACCTCCATAGAAGACACCGGGACC

GATCCAGCCTCCGCGGCCCGCGCACGGCAAGAGGCGAGGGGCGGCGAC

TGAATTGGGTGTCGACCAGCCACCATGGAGACAGACACACTCCTGCTA

TGGGTACTGCTGCTCTGGGTTCCAGGTTCCACTGGTGACGCGGCCTAT

ACCAGCCTGATTCATAGCCTGATTGAAGAAAGCCAGAACCAGCAGGAA

AAAAACGAACAGGAACTGCTGGAACTGGATAAATGGGCGAGCCTGTGG

AACTGGTTTTGAGAATTCATCGAGTAACTATTGTGTCATGCAACATAA

ATAAACTTATTGTTTCAACACCTACTAATTGTGCTGCAGGGGCCCGCC

CCAACTGGGGTAACCTTTGAGTTCTCTCAGTTGGGGGTAATCAGCATC

ATGATGTGGTACCACATCATGATGCTGATTATAAGAATGCGGCCGCCA

CACTCTAGTGGATCTCGAGTTAATAATTCAGAAGAACTCGTCAAGAAG

GCGATAGAAGGCGATGCGCTGCGAATCGGGAGCGGCGATACCGTAAAG

CACGAGGAAGCGGTCAGCCCATTCGCCGCCAAGCTCTTCAGCAATATC

ACGGGTAGCCAACGCTATGTCCTGATAGCGGTCCGCCACACCCAGCCG

GCCACAGTCGATGAATCCAGAAAAGCGGCCATTTTCCACCATGATATT

CGGCAAGCAGGCATCGCCATGGGTCACGACGAGATCCTCGCCGTCGGG

CATGCTCGCCTTGAGCCTGGCGAACAGTTCGGCTGGCGCGAGCCCCTG

ATGCTCTTCGTCCAGATCATCCTGATCGACAAGACCGGCTTCCATCCG

AGTACGTGCTCGCTCGATGCGATGTTTCGCTTGGTGGTCGAATGGGCA

GGTAGCCGGATCAAGCGTATGCAGCCGCCGCATTGCATCAGCCATGAT

GGATACTTTCTCGGCAGGAGCAAGGTGTAGATGACATGGAGATCCTGC

CCCGGCACTTCGCCCAATAGCAGCCAGTCCCTTCCCGCTTCAGTGACA

ACGTCGAGCACAGCTGCGCAAGGAACGCCCGTCGTGGCCAGCCACGAT

AGCCGCGCTGCCTCGTCTTGCAGTTCATTCAGGGCACCGGACAGGTCG

GTCTTGACAAAAAGAACCGGGCGCCCCTGCGCTGACAGCCGGAACACG

GCGGCATCAGAGCAGCCGATTGTCTGTTGTGCCCAGTCATAGCCGAAT

AGCCTCTCCACCCAAGCGGCCGGAGAACCTGCGTGCAATCCATCTTGT

TCAATCATGCGAAACGATCCTCATCCTGTCTCTTGATCAGAGCTTGAT

CCCCTGCGCCATCAGATCCTTGGCGGCGAGAAAGCCATCCAGTTTACT

TTGCAGGGCTTCCCAACCTTACCAGAGGGCGCCCCAGCTGGCAATTCC

GGTTCGCTTGCTGTCCATAAAACCGCCCAGTCTAGCTATCGCCATGTA

AGCCCACTGCAAGCTACCTGCTTTCTCTTTGCGCTTGCGTTTTCCCTT
```

-continued
```
GTCCAGATAGCCCAGTAGCTGACATTCATCCGGGTCAGCACCGTTTC
TGCGGACTGGCTTTCTACGTGCTCGAGGGGGGCCAAACGGTCTCCAGC
TTGGCTGTTTTGGCGGATGAGAGAAGATTTTCAGCCTGATACAGATTA
AATCAGAACGCAGAAGCGGTCTGATAAAACAGAATTTGCCTGGCGGCA
GTAGCGCGGTGGTCCCACCTGACCCCATGCCGAACTCAGAAGTGAAAC
GCCGTAGCGCCGATGGTAGTGTGGGGTCTCCCCATGCGAGAGTAGGGA
ACTGCCAGGCATCAAATAAAACGAAAGGCTCAGTCGAAAGACTGGGCC
TTTCGTTTTATCTGTTGTTTGTCGGTGAACGCTCTCCTGAGTAGGACA
AATCCGCCGGGAGCGGATTTGAACGTTGCGAAGCAACGGCCCGGAGGG
TGGCGGGCAGGACGCCCGCCATAAACTGCCAGGCATCAAATTAAGCAG
AAGGCCATCCTGACGGATGGCCTTTTTGCGTTTCTACAAACTCTTTTG
TTTATTTTTCTAAATACATTCAAATATGTATCCGCTCATGACCAAAAT
CCCTTAACGTGAGTTTTCGTTCCACTGAGCGTCAGACCCCGTAGAAAA
GATCAAAGGATCTTCTTGAGATCCTTTTTTTCTGCGCGTAATCTGCTG
CTTGCAAACAAAAAAACCACCGCTACCAGCGGTGGTTTGTTTGCCGGA
TCAAGAGCTACCAACTCTTTTTCCGAAGGTAACTGGCTTCAGCAGAGC
GCAGATACCAAATACTGTCCTTCTAGTGTAGCCGTAGTTAGGCCACCA
CTTCAAGAACTCTGTAGCACCGCCTACATACCTCGCTCTGCTAATCCT
GTTACCAGTGGCTGCTGCCAGTGGCGATAAGTCGTGTCTTACCGGGTT
GGACTCAAGACGATAGTTACCGGATAAGGCGCAGCGGTCGGGCTGAAC
GGGGGGTTCGTGCACACAGCCCAGCTTGGAGCGAACGACCTACACCGA
ACTGAGATACCTACAGCGTGAGCTATGAGAAAGCGCCACGCTTCCCGA
AGGGAGAAAGGCGGACAGGTATCCGGTAAGCGGCAGGGTCGGAACAGG
AGAGCGCACGAGGGAGCTTCCAGGGGGAAACGCCTGGTATCTTTATAG
TCCTGTCGGGTTTCGCCACCTCTGACTTGAGCGTCGATTTTTGTGATG
CTCGTCAGGGGGCGGAGCCTATGGAAAAACGCCAGCAACGCGGCCTT
TTTACGGTTCCTGGCCTTTTGCTGGCCTTTTGCTCACATGTTCTTTCC
TGCGTTATCCCCTGATTCTGTGGATAACCGTATTACCGCCTTTGAGTG
AGCTGATACCGCTCGCCGCAGCCGAACGACCGAGCGCAGCGAGTCAGT
GAGCGAGGAAGCGGAAGAGCGCCTGATGCGGTATTTTCTCCTTACGCA
TCTGTGCGGTATTTCACACCGCATATGGTGCACTCTCAGTACAATCTG
CTCTGATGCCGCATAGTTAAGCCAGTATACACTCCGCTATCGCTACGT
GACTGGGTCATGGCTGCGCCCCGACACCCGCCAACACCCGCTGACGCG
CCCTGACGGGCTTGTCTGCTCCCGGCATCCGCTTACAGACAAGCTGTG
ACCGTCTCCGGGAGCTGCATGTGTCAGAGGTTTTCACCGTCATCACCG
AAACGCGCGAGGCAGCAGATCAATTCGCGCGCGAAGGCGAAGCGGCAT
GCATAATGTGCCTGTCAAATGGACGAAGCAGGGATTCTGCAAACCCTA
TGCTACTCCGTCAAGCCGTCAATTGTCTGATTCGTTACCAATTATGAC
AACTTGACGGCTACATCATTCACTTTTTCTTCACAACCGGCACGGAAC
TCGCTCGGGCTGGCCCCGGTGCATTTTTTAAATACCCGCGAGAAATAG
AGTTGATCGTCAAAACCAACATTGCGACCGACGGTGGCGATAGGCATC
```
-continued
```
CGGGTGGTGCTCAAAAGCAGCTTCGCCTGGCTGATACGTTGGTCCTCG
CGCCAGCTTAAGACGCTAATCCCTAACTGCTGGCGGAAAAGATGTGAC
AGACGCGACGGCGACAAGCAAACATGCTGTGCGACGCTGGCGAT
```

T20

(SEQ ID NO: 2)

YTSLIHSLIEESQNQQEKNEQELLELDKWASLWNWF

The MC was transfected into HeLa, Hek and U2OS cells using lipofectamine according to the manufacturer's protocol, adding 24 µg of vector to a 10 cm plate. FIG. 1 shows the expression of ssT20 in vitro 48 hours after transfection, both in an immunoprecipitated sample and in crude cell lysate. The prominent bands of larger molecular weight are the heavy and light chain of the antibody used in immunoprecipitation. As the same antibody was used for the western blot, also these were detected by the secondary antibody. This study shows that it is feasible to produce the T20 peptide in transfected human cells.

T20 has previously been expressed as a multimeric fusion protein, which was shown to have an antiviral effect in vitro (Hacein-Bey-Abina et al., 2008, J Clin Invest 118:3132-42). Dervillez et al. (2006, Chem Med Chem 1:330-39) also expressed the C46 peptide, a T20 derived peptide, alone and showed expression but no secretion of the peptide. However, they did not study the immunogenicity of their peptide construct. For immunostimulation, secretion is not crucial, since transfected cells can present the antigen on MHC molecules. T20 can therefore be recognized as foreign and trigger an immune response. Here, we showed that the MC vector can express the monomeric T20 peptide in human cell lines, and the protein was detectable by western blotting using the neutralizing human antibody 2F5.

Subsequent efforts were directed to improving the purity of the MC product. We analysed a number of different bacterial strains, and found that using the O17 E. coli strain, known for its high protein production efficiency, resulted in improved recombination and degradation. We also tried co-fermenting the MC plasmid with a plasmid constitutively expressing arabinose import, but it was difficult to balance copy number rate of the two plasmids in the bacteria.

In order to produce quantities required for clinical use, the process needs to be scaled up from shaking incubators to fermentor scale. A pilot plant scale fermentation experiment on the first generation MC system was performed with 5 liters of medium in a NOVAFERM® (Falkenberg, Sweden) fermentor. The parental plasmid was grown overnight, and then minicircle formation was induced by injection of arabinose. Growth was continued for four hours. One 5 liter fermentation batch gave 65 mg of product, but it had a very high content of unrecombined and undigested plasmids, containing only 15% MC. This initial scale up study of the MC production system showed that a high yield of plasmid can be obtained, but improvements were needed to reach higher purity in the final product.

After Kay et al. (2010, Nature Biotech 28:1287-89) disclosed their improved system with the specialized ZYCY10P3S2T bacterial strain, further studies utilized MC formation in ZYCY10P3S2T. Using this system, the yield of small MC vectors was improved by adding L-arabinose at several time points during the induction phase of the fermentation, to mimic a fed-batch fermentation. The new T20 MC production method provides high yield of relatively pure T20 MC.

Example 3. T20 Microcircle-Based Vaccine

The T20 MC is of use as a vaccine system to inhibit or prevent HIV infection. T20 blocks the early membrane fusion step in the virus life cycle and can prevent de novo infection and cell-to-cell virus transmission. Although it has been previously shown that anti-gp41 antibodies do not impair the antiviral effects of T20 in the treatment of HIV, little was known about the immunoprotective properties of T20 itself (Walmsley et al., 2003, J Infect Dis 188:1827-33). The T20 peptide can be recognized as an HIV antigen since it contains the broadly reactive 2F5 epitope (Muster et al., 1993, J Virol 67:6642-47). This immunoreactive activity of the T20 peptide results from the fact that the peptide mimics residues 643-678 of the HIV-1 glycoprotein gp41. Thus, any antibodies or CTL reactivity formed against the T20 peptide will also bind to this critical region of the HIV-1 transmembrane protein. Natural antibody responses to gp41 and gp120 occur soon after HIV-infection, and can result in neutralizing antibodies.

Figure 2:
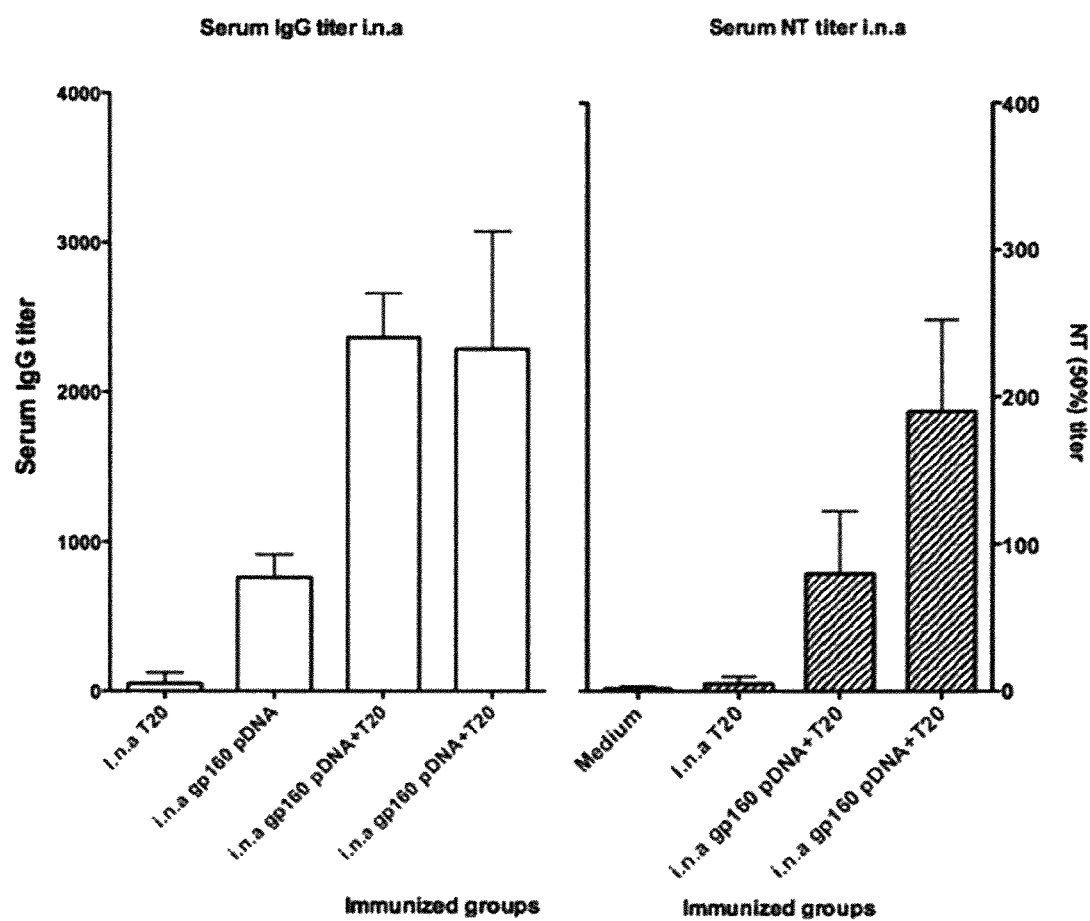
FIG. 2 shows a comparison of intranasal (i.n.a) deposition of medium, T20 peptide alone, DNA vaccine plasmid gp160 alone or T20 mixed with plasmid gp160. T20 peptide mixed with the plasmid appears to enhance both serum IgG titres of binding to gp160 as well as neutralizing antibodies (NT) to HIV-1 subtype B.

The T20 peptide was evaluated as a part of an HIV protein/DNA vaccine (FIG. 2). FIG. 2 shows that administering the T20 peptide together with HIV-1 DNA vaccine constructs enhances anti-Env immunogenicity. Therefore, we cloned the T20 coding sequence and an expression cassette previously used in HIV inhibition studies (Calarota et al., 1998, Lancet 351:1320-25) into the pMC-vector for MC-production. The construct containing the T20 coding sequence was as disclosed in Chang et al. (2012, PLoS One 7:e41235).

Example 4. Use of DDD Moiety to Enhance Immunogenicity

In certain embodiments, the ability to induce an immune response against HIV infection may be enhanced by administering T20, or other viral antigens, in combination with one or more adjuvant agents. By enhancing the general immune response, adjuvants can promote a more effective induction of a specific immune response against a targeted antigen, such as T20.

A fusion protein (encoded by SEQ ID NO:3) was constructed comprising a DDD2 moiety (SEQ ID NO:5) joined to the T20 sequence (SEQ ID NO:2) via a hinge linker (encoded by SEQ ID NO:15, with a (His)$_6$GS (SEQ ID NO:16) moiety added for use in affinity chromatography. The structure of the overall fusion protein is shown in FIG. 3.

The DDD-containing construct with T20 fusion protein is referred to herein as a "T20 plasmid" to distinguish from the non-DDD containing T20 MC. An experiment is performed that demonstrates that fusion of antigen (e.g, T20) to the DDD moiety enhances the potency of DNA vaccines to produce antigen-specific antibodies in immunized subjects.

Although the mechanism of action by which DDD enhances potency of a DNA vaccine is presently unknown, a possible explanation is that the DDD-T20 protein expressed in DCs binds to AKAPs in the lipid raft, which facilitates the antigen presentation of T20, resulting in a notable increase of anti-T20 antibodies. Schillace et al (2009, PLoS One e4807; 2011, Immunol Cell Biol 89:650-58) reported the requirement of dendritic cell (DC) AKAPs for antigen presentation, but contained no disclosure or suggestion relating to use of DDD-antigen fusion proteins with DNA vaccines to increase the production of antigen-specific antibodies. Instead, inhibitors to AKAP were used by Schillace to prevent antigen presentation in DCs.

This hypothesis may be tested with various DNA vaccines comprising fused DDD-X genes. Exemplary choices of X include, but are not limited to, T20, the A3B3 domain of CEACAM5, the extracellular domain of CD20, PD-L1, and PD-1 proteins. Such DNA vaccines can be generated by cloning the fused DDD-X gene into pKCMV, a commercially available plasmid. The subject DNA vaccines have the advantages of low cost, easy construction, and cross presentation of both class I and II antigens.

While the DDD2 moiety (SEQ ID NO:5) is used for initial fusion protein constructs, other known DDD moieties may be incorporated in the subject fusion proteins, expression vectors and vaccines. For example, DDD1 (SEQ ID NO:4) may also be utilized and may be as effective as DDD2, if not more.

An exemplary immunization schedule for DNA vaccines in BALB/C mice is shown below. The term "PlasmidsEnv subtype A, B and C" is as disclosed in Nilsson et al. (2015, PLoS ONE) and refers to DNA plasmids encoding HIV-1 genes gp160 subtypes A, B and C. The minicircle T20 and plasmidT20 are as disclosed above. Mice are immunized at 0, 4, and 8 weeks.

Immunization Schedule of BALB/C Mice
Group A:
PlasmidsEnv subtype A, B, and C (20 μg)+minicircle T20 (20 μg)
Group B:
PlasmidsEnv subtype A, B, and C (20 μg)+plasmidT20 (20 μg)
Group C:
PlasmidsEnv subtype A, B, and C (20 μg)+T20 protein (10 μg)
Group D:
PlasmidsEnv subtype A, B, and C (20 μg)+empty pKCMV (20 μg)
Group E:
Empty plasmid pKCMV (40 μg)

Figure 4:
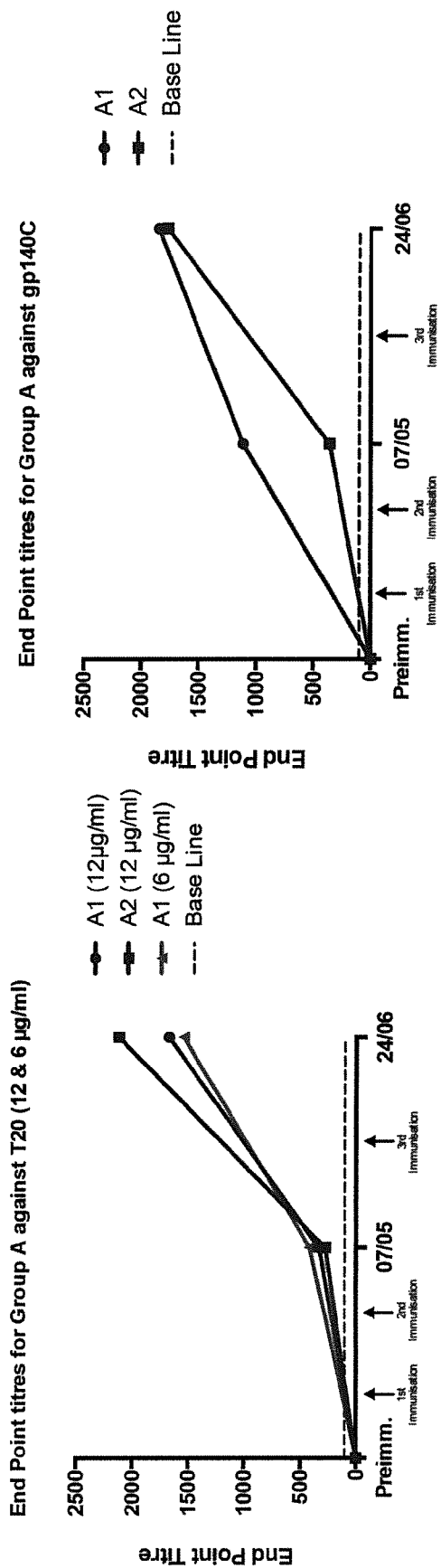
FIG. 4 shows the production of anti-T20 and anti-gp140C antibodies in mice immunized in Group A after three immunizations. ELISA was performed with T20 and gp140C antigens, incubated with sera from Group A mice. The results indicate that the PlasmidsEnv+minicircle T20 is successful in producing both gp140C and T20 specific antibodies, and that the titre is increased by approx. 5-fold after the 3$^{rd}$ immunization.
Figure 5:
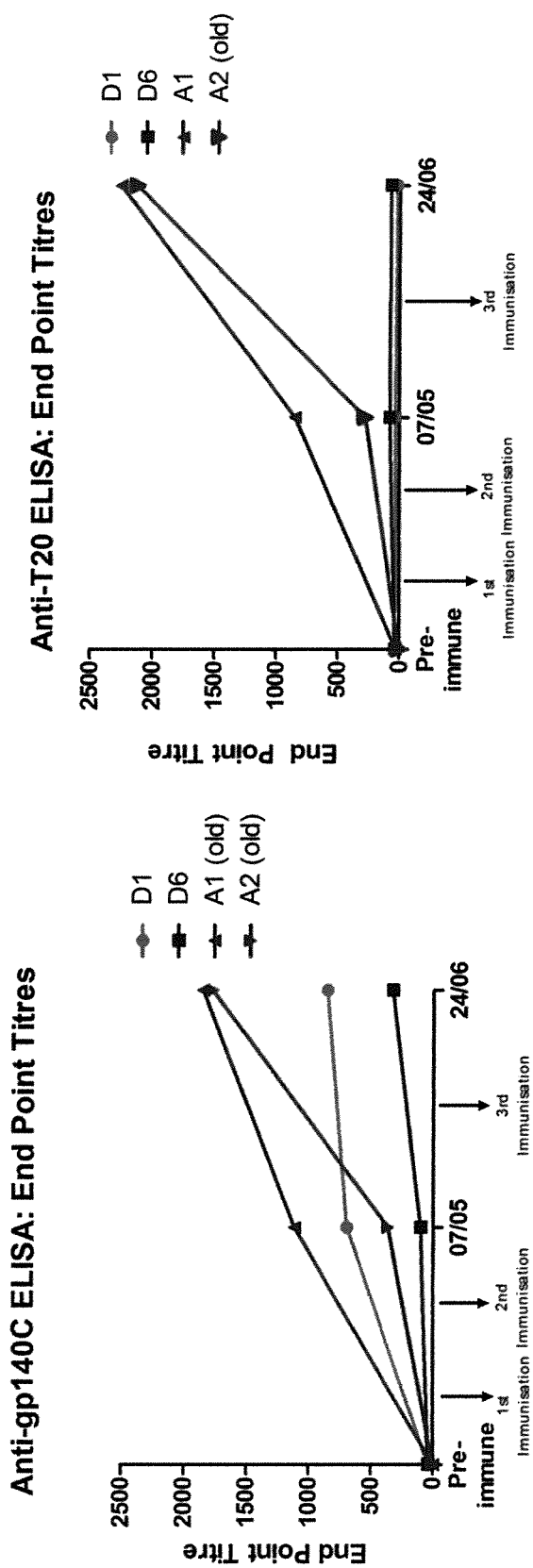
FIG. 5 shows a comparison between mice immunized in Group A (PlasmidEnv A, B and C+T20 MC) vs. Group D (PlasmidEnv A, B and C+empty pKCMV vector). ELISA was performed as in the legend to FIG. 4.

A comparison was performed between Group A and Group D mice, immunized as shown above. FIG. 4 shows the production of anti-T20 and anti-gp140C antibodies in mice immunized in Group A after three immunizations. The results indicate that the PlasmidsEnv+minicircle T20 is successful in producing both gp140C and T20 specific antibodies, and that the titre is increased by approx. 5-fold after the 3$^{rd}$ immunization. FIG. 5 shows that the immune response was dependent on the presence of T20 expression in immunized mice. Mice immunized in Group A (PlasmidEnv A, B and C+T20 MC) vs. Group D (PlasmidEnv A, B and C+empty pKCMV vector) were compared for the presence of antibodies against T20 and gp140C, after 3 immunizations. The results show that the minicircle T20 in combination with plasmidsEnv was successful in producing T20 antibodies, whereas the plasmidsEnv alone failed to induce doing so. Although mice in Group D produced low titers of antibodies against gp140C, the level of antibody production increased substantially when T20 MC was added.

A further experiment is performed, as outlined above, to compare the induction of immune response against T20 and gp140C. It is observed that, in comparing mice immunized in Group A (with T20, without DDD2) vs. Group B (with T20, with DDD2), the addition of the DDD2 (SEQ ID NO:5) moiety as a fusion protein with T20, the vaccine resulted in an 8-fold higher antibody titer level, compared to the identical immunization in the absence of DDD2. Thus, addition of DDD2 to the T20 MC vaccine was effective to promote formation of antibodies against T20 and gp140C.

Example 5. In Vivo Peptide Production and Gene Therapy with a T20 MC Construct Treatment of ischemic tissue with growth factors such as VEGF had shown promising results in animal experiments but clinical trials were disappointing (Henry et al., 2003, Circulation 107:1359-65). This was in part attributed to the short half-life of the growth factor in vivo. Problems preventing successful clinical application of gene therapy for cardiac diseases were related to inefficient gene transfer, host immune responses, and the lack of sustainable therapeutic transgene expression.

As the MC construct addresses at least two of these problems, a study is performed to compare the expression of T20 protein from an MC vector to plasmid constructs. A plasmid vector, used in pre-clinical studies, is compared to the MC-parental plasmid and T20 MC construct, disclosed in Example 2 above. The constructs are delivered by direct intramuscular injection of naked DNA. The T20 MC vector, containing the same expression cassette as the parental plasmid but encompassing only 1.1 kbp, shows increased transfection and protein expression in vivo, allowing use of T20 MC for gene therapy in HIV.

These results are consistent with those reported for MC-based gene therapy in other model systems. Lijkwan et al. (2014, Hum Gene Ther 25:41-49) used luciferase as a reporter gene to compare expression from equimolar treatment with MC and a plasmid construct in mouse skeletal muscle. They reported significantly higher expression from the MC for up to 28 days. Huang et al. (2009, Circulation 130:S60-69) performed a similar comparison in murine heart. In heart, the MC had a higher expression than the plasmid and luciferase was detectable for 90 days. When using the therapeutically more relevant HIF-1α protein, Huang et al. (2009) were able to detect significant expression from the MC vector 14 days after treatment, with levels more than twice those of the plasmid construct.

The smaller size, the absence of antibiotic resistance gene and lower CpG content make the MC a useful alternative for gene therapy treatment.

Example 6. MC Delivery Methods

The MC construct may be delivered by different alternative methods for therapeutic use. Our work indicates that electroporation can be a suitable method to enhance delivery of the MC into host tissues. The vector itself may also be modified for delivery by electroporation. A sequence that has been shown to increase gene expression in smooth muscle after electroporation is a region of the smooth muscle γ-actin promoter (Young et al., 2008, Exp Biol Med 233:840-48). It contains a tissue specific transcription factor binding site which drives nuclear accumulation of the vector.

Hydrodynamic perfusion of hind limb is another method that has been used successfully for delivery to muscle of viral vectors and ASO as well as for plasmids. However, neither hydrodynamics nor electroporation would be a realistic tool for systemic delivery throughout the body. These methods would be more suitable for localized delivery of vectors for treatment. Where the T20 MC is utilized, for example, as a vaccine system to induce systemic immune response against T20, and ultimately gp41 and intact HIV or HIV-infected cells, localized delivery will be effective for immune system activation, which will then provide systemic protection against HIV. An efficiently transfected muscle could in principle also be used as production site for a secreted therapeutic protein that could have its target elsewhere in the body, such as T20 (envufirtide). As the skeletal muscle cells are not dividing, the vector would be present in the tissue for a long time.

Hydrodynamics has also been used in several studies for delivery of MC to the liver of mice, and has shown a higher and more robust expression as compared to plasmid. Ultrasound is another physical method that has been used for gene delivery of MC vectors, targeting the salivary glands of mice (Geguchadze et al., 2014, Meth Clin Dev 1:14007). The study reported that the MC vector had an increased expression of luciferase as compared to a conventional plasmid. Compared with MC vector, transfection with plasmid caused a change of protein content, especially in pathways associated with immunity, cellular stress, and morphogenesis. These effects were substantially decreased when using the MC as a gene delivery vector. The plasmid backbone induces an immunological response similar to that seen when using viral vectors. Thus the MC vector enables a higher expression and is also less toxic than a full-length plasmid vector.

Chemical delivery is another approach to achieve more efficient delivery of nonviral vectors. Chemical delivery refers to the use of different carrier lipids or peptides to condense and protect the DNA and enhance cellular uptake. There are numerous studies on optimizing the chemistry of the carrier, as well as coupling it to signal moieties for improved uptake and intracellular traffic. These can be nuclear localization signals or cell binding ligands. Such ligands can also promote targeting of the vector to a given organ. The use of cell penetrating peptides, covalently or non-covalently attached to the cargo, can facilitate entry into cells. As an example of how these methods can be combined, Ko et al. (2009, Gene Ther 16:52-59) reported that targeted gene delivery to ischemic myocardium by intravenous injection in rats was enhanced when pDNA and lipid complexes were modified with cell penetrating peptides and a monoclonal antibody specific for cardiac myosin.

Example 7. DNA Vaccination

With the limitations of systemic delivery efficiency, the T20 MC might be more suitable for use when only local expression is needed. One such situation is DNA vaccination, where the antigen is commonly delivered to a small area intradermally or intramuscularly. Electroporation has been shown to be an efficient delivery method for eliciting strong immune responses in humans (Sallberg et al., 2015, Med Microbiol Immunol 204:131-35). Both the increased DNA uptake and the local tissue damage acting as an adjuvant is believed to improve immunization. As discussed above, the T20 MC could be a more optimal vector for delivery with electroporation than a conventional plasmid, due to its smaller size. Another benefit of the smaller size is the increased therapeutic dose per μg DNA when using MCs as compared to normal plasmids. This is of importance as high local transgene expression is crucial for a good immune response.

One feature of plasmid DNA that is thought to induce an immune response is the high content of unmethylated CpGs, which can act as adjuvant for vaccines. An MC vector for DNA vaccination will have less CpGs than a conventional plasmid, due to its smaller size. However, optimized CpG sequences may be cloned into to the MC cassette. Coban et al. (2005, J Leuk Biol 78:647-55), have shown that inclusion of certain optimized CpG sequences in a plasmid enhanced the immune response in mice. These sequences were only between 30 and 50 bp so the resulting MC would still be considerably smaller than a conventional plasmid. Alternatively, the MC could be delivered together with synthetic CpG oligonucleotides. Co-administering CpG oligonucleotides with a variety of vaccine agents has improved the humoral and cellular immune responses (Klinman et al., 2009, Adv Drug Delivery Rev 61:248-55). For DNA vaccine purposes, it could very well be an advantage to not have the adjuvant covalently attached to the DNA sequence from which the antigen is to be expressed.

Example 8. Ex Vivo Therapy

Ex vivo therapy can be viewed as an example of local therapeutic gene expression. Ex vivo treatment aims to remove cells (e.g., dendritic cells) from a patient, modify them in the laboratory and then return the modified cells to the patient where they affect the disease. For ex vivo use, it could be beneficial to use a high therapeutic dose of a non-integrating vector devoid of any resistance genes, which could be transferred back to the patient. Evans and Hyde (2015, Rheumatology 11:234-42) reviewed several gene therapy approaches to regenerate the musculoskeletal system, among them ex vivo strategies mainly using viral vectors. Usas et al. (2007, Biomaterials 28:5401-06) studied muscle derived stem cells and their modification ex vivo, e.g. using retroviral vectors to enhance bone formation. They also modified the stem cells with a combination of growth factors, such as VEGF, which enhanced bone generation. Sheyn et al. (2008, Stem Cells 26:1056-64) used adipose tissue-derived stem cells modified ex vivo with a plasmid vector to enhance bone formation and spinal fusion. They concluded that the nonviral gene delivery method used to genetically engineer the stem cells ex vivo is safe and transient, limiting overexpression of the osteogenic gene to a period of a few weeks. The MC vector has also been used ex vivo in human adipose-derived stromal cells, to induce a transient overexpression of the Bcl-2 prosurvival protein (Hyun et al., 2013, Stem Cells Transl Med 2:690-702). This enhanced cell survival and bone formation upon implantation into a mouse model, and expression was seen for up to four weeks.

In certain embodiments, such as for inducing a host immune against HIV, ex vivo delivery of T20 MC to antigen-presenting cells, such as dendritic cells, may be used in the practice of the claimed methods.

All of the COMPOSITIONS and METHODS disclosed and claimed herein can be made and executed without undue experimentation in light of the present disclosure. While the compositions and methods have been described in terms of preferred embodiments, it is apparent to those of skill in the art that variations maybe applied to the COMPOSITIONS and METHODS and in the steps or in the sequence of steps of the methods described herein without departing from the concept, spirit and scope of the invention. More specifically, certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. An isolated nucleic acid comprising a nucleic acid sequence selected from the group consisting of SEQ ID NO:1 and SEQ ID NO:3 that expresses T20 or a T20 fusion protein.

2. A T20 expression vector comprising the nucleic acid sequence of SEQ ID NO:1 or SEQ ID NO:3.

3. The expression vector of claim 2, wherein the expression vector is a minicircle vector.

4. An expression vector that expresses a fusion protein comprising:
   a) a T20 peptide; and
   b) a dimerization and docking domain (DDD) peptide from a human protein kinase A (PKA) regulatory subunit.

5. The expression vector of claim 4, wherein the regulatory subunit is RIα, RIβ, RIIα or RIIβ.

6. The expression vector of claim 4, wherein the DDD peptide is DDD1 (SEQ ID NO:4), DDD2 (SEQ ID NO:5), DDD3 (SEQ ID NO:8) or DDD3C (SEQ ID NO:9).

7. A vaccine comprising a T20 expression vector according to claim 2.

8. A vaccine comprising an expression vector according to claim 4.

9. A pharmaceutical composition comprising a T20 expression vector according to claim 2.

10. A pharmaceutical composition comprising a T20 peptide (SEQ ID NO:2) expressed from a T20 expression vector according to claim 2.

11. A method of use of a T20 expression vector comprising:
   a) obtaining human dendritic cells (DCs);
   b) transfecting the human DCs with a T20 expression vector according to claim 2; and
   c) administering the transfected DCs to a human subject.

12. The method of claim 11, wherein the human DCs are autologous DCs isolated from the human subject.

13. The method of claim 11, wherein the human DCs are allogeneic DCs.

14. The method of claim 11, further comprising exposing the DCs to an adjunct compound selected from the group consisting of lipopolysaccharide, GM-CSF and interferon-α.

15. The method of claim 11, further comprising administering at least one anti-HIV agent to the subject.

16. The method of claim 15, wherein the anti-HIV agent is selected from the group consisting of HAART, a reverse transcriptase inhibitor, a fusion inhibitor, a protease inhibitor, an integrase inhibitor and an anti-HIV antibody.

17. The method of claim 15, wherein the anti-HIV agent is selected from the group consisting of 4,4-difluoro-N-

((1S)-3-(exo-3-(3-isopropyl-5-methyl-4H-1,2,4-triazol-4-yl)-8-azabicyclo(3.2.1)oct-8-yl)-1-phenylpropyl)cyclohexanecarboxamide, abacavir, amdoxovir, amprenavir, AOP-RANTES, apricitabine, atazanavir, bevirimat, BMS-378806, BMS-488043, C34, C52L, calanolide A, CCR5, a CCR5 antagonist, CD4, ceragenin, cobicistat, CP32M, cyanovirin-N, darunavir, DCM205, diarylpyrimidines, didanosine, dolutegravir, efavirenz, elvitegravir, elvucitabine, emtricitabine, enfuvirtide, epigallotachen gallate, etravirine, festinavir, fosamprenavir, foscarnet, griffithsin, globoidnan A, hydroxycarbamide, indinavir, IZN17, JM 3100, KP-146, KRV2110, lamivudine, lefinavir, lersivirine, lopinavir, maraviroc, miltefosine, MK-2048, nelfinavir, nevirapine, plerixafor, PRO 140, racivir, raltegravir, rilpivirine, ritonavir, saquinavir, sCD4-D1-D2, selicicib, stafudine, stampidine, stavudine, T20, T61, T1144, T651, T1249, T2635, TAK 779, TAK-220, Tat antagonists, tenofovir, tipranavir, TNX-355, trichosanthin, TRIM5alpha, vicriviroc, vivecon, zalcitabine, zidovudine and zidovudine.

18. The method of claim 16, wherein the anti-HIV antibody is selected from the group consisting of ibalizumab, anti-Leu3a, L120, OKT4A, 13B8.2, L71, NBP1-43335, ab10397, 2D7, HGS004, MC-1, MC-4, MC-5, PA9, PA14, PRO140, 2G12, 2F5, 3D6, b12, C37, E4D10, 1ACY, 1F58, 1GGGC, VRC01, HJ16, 17b and P4/D10.

19. A method of use of a T20 expression vector comprising:
    a) administering a T20 expression vector to a human subject; and
    b) transfecting cells in the human subject with the T20 expression vector;

wherein the transfected cells express T20 peptide (SEQ ID NO:2).

20. The method of claim 19, wherein the T20 peptide is secreted into the subject's circulation.

21. The method of claim 20, wherein the T20 peptide inhibits HIV infection of the subject.

22. The method of claim 20, wherein the T20 peptide prevents HIV infection of the subject.

23. The method of claim 19, wherein the transfected cells induce an immune response in the subject against T20, gp41 and HIV.

24. The method of claim 23, wherein the immune response is effective to prevent HIV infection of the subject.

25. The method of claim 23, wherein the immune response is effective to kill HIV-infected cells in the subject.

26. A method of producing T20 peptide comprising:
    a) obtaining a T20 expression vector according to claim 2;
    b) transfecting a cell line with the T20 expression vector; and
    c) culturing transfected cells to produce T20 peptide.

27. A method of producing a T20 MC expression vector comprising:
    a) providing a T20 expression plasmid;
    b) transfecting a ZYCY10P3S2T bacterial strain with the T20 expression plasmid;
    c) exposing the transfected bacterial strain to arabinose to induce recombinase activity; and
    d) producing the T20 MC expression vector.

* * * * *

SEQUENCE LISTING

```
<160> NUMBER OF SEQ ID NOS: 16

<210> SEQ ID NO 1
<211> LENGTH: 5132
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
acattaccct gttatcccta gatgacatta ccctgttatc ccagatgaca ttaccctgtt      60
atccctagat gacattaccc tgttatccct agatgacatt accctgtta tccctagatg     120 acattaccct gttatcccag atgacattac cctgttatcc ctagatacat taccctgtta     180
tcccagatga catacctgt tatccctaga tgacattacc ctgttatccc agatgacatt     240
accctgttat ccctagatac attaccctgt tatcccagat gacataccct gttatccta     300 gatgacatta ccctgttatc ccagatgaca ttaccctgtt atccctagat acattaccct     360
gttatcccag atgacatacc ctgttatccc tagatgacat taccctgtta tcccagatga     420
cattaccctg ttatccctag atacattacc ctgttatccc agatgacata ccctgttatc     480
cctagatgac attaccctgt tatcccagat gacattaccc tgttatccct agatacatta     540
ccctgttatc ccagatgaca taccctgtta tccctagatg acattaccct gttatcccag     600
atgacattac cctgttatcc ctagatacat taccctgtta tcccagatga catacctgt     660 tatccctaga tgacattacc ctgttatccc agataaactc aatgatgatg atgatgatgg     720
tcgagactca gcggccgcgg tgccagggcg tgcccttggg ctccccgggc gcgactagtg     780
```

```
aattcagatc tgatatctct agaggcccat tgcatacgtt gtatccatat cataatatgt    840
acatttatat tggctcatgt ccaacattac cgccatgttg acattgatta ttgactagtt    900
attaatagta atcaattacg gggtcattag ttcatagccc atatatggag ttccgcgtta    960
cataacttac ggtaaatggc ccgcctggct gaccgcccaa cgaccccgc ccattgacgt    1020
caataatgac gtatgttccc atagtaacgc caatagggac tttccattga cgtcaatggg    1080
tggagtattt acggtaaact gcccacttgg cagtacatca agtgtatcat atgccaagta    1140
cgccccctat tgacgtcaat gacggtaaat ggcccgcctg gcattatgcc cagtacatga    1200
ccttatggga ctttcctact tggcagtaca tctacgtatt agtcatcgct attaccatgg    1260
tgatgcggtt ttggcagtac atcaatgggc gtggatagcg gtttgactca cggggatttc    1320
caagtctcca ccccattgac gtcaatggga gtttgttttg gcaccaaaat caacgggact    1380
ttccaaaatg tcgtaacaac tccgccccat tgacgcaaat gggcggtagg cgtgtacggt    1440
gggaggtcta tataagcaga gctcgtttag tgaaccgtca gatcgcctgg agacgccatc    1500
cacgctgttt tgacctccat agaagacacc gggaccgatc cagcctccgc ggcccgcgca    1560
cggcaagagg cgaggggcgg cgactgaatt gggtgtcgac cagccaccat ggagacagac    1620
acactcctgc tatgggtact gctgctctgg gttccaggtt ccactggtga cgcggcctat    1680
accagcctga ttcatagcct gattgaagaa agccagaacc agcaggaaaa aaacgaacag    1740
gaactgctgg aactggataa atgggcgagc ctgtggaact ggttttgaga attcatcgag    1800
taactattgt gtcatgcaac ataaataaac ttattgtttc aacacctact aattgtgctg    1860
caggggcccg ccccaactgg ggtaacccttt gagttctctc agttggggt aatcagcatc    1920
atgatgtggt accacatcat gatgctgatt ataagaatgc ggccgccaca ctctagtgga    1980
tctcgagtta ataattcaga agaactcgtc aagaaggcga tagaaggcga tgcgctgcga    2040
atcgggagcg gcgataccgt aaagcacgag gaagcggtca gcccattcgc cgccaagctc    2100
ttcagcaata tcacgggtag ccaacgctat gtcctgatag cggtccgcca cacccagccg    2160
gccacagtcg atgaatccag aaaagcggcc attttccacc atgatattcg gcaagcaggc    2220
atcgccatgg gtcacgacga gatcctcgcc gtcgggcatg ctcgccttga gcctggcgaa    2280
cagttcggct ggcgcgagcc cctgatgctc ttcgtccaga tcatcctgat cgacaagacc    2340
ggcttccatc cgagtacgtg ctcgctcgat gcgatgtttc gcttggtggt cgaatgggca    2400
ggtagccgga tcaagcgtat gcagccgccg cattgcatca gccatgatgg atactttctc    2460
ggcaggagca aggtgtagat gacatggaga tcctgccccg gcacttcgcc caatagcagc    2520
cagtcccttc ccgcttcagt gacaacgtcg agcacagctg cgcaaggaac gcccgtcgtg    2580
gccagccacg atagccgcgc tgcctcgtct tgcagttcat tcagggcacc ggacaggtcg    2640
gtcttgacaa aaagaaccgg gcgcccctgc gctgacagcc ggaacacggc ggcatcagag    2700
cagccgattg tctgttgtgc ccagtcatag ccgaatagcc tctccaccca gcggccgga    2760
gaacctgcgt gcaatccatc ttgttcaatc atgcgaaacg atcctcatcc tgtctcttga    2820
tcagagcttg atcccctgcg ccatcagatc cttggcggcg agaaagccat ccagtttact    2880
ttgcagggct tcccaacctt accagagggc gccccagctg gcaattccgg ttcgcttgct    2940
gtccataaaa ccgcccagtc tagctatcgc catgtaagcc cactgcaagc tacctgcttt    3000
ctctttgcgc ttgcgttttc ccttgtccag atagcccagt agctgacatt catccggggt    3060
cagcaccgtt tctgcggact ggctttctac gtgctcgagg ggggccaaac ggtctccagc    3120
ttggctgttt tggcggatga gagaagattt tcagcctgat acagattaaa tcagaacgca    3180
```

-continued

```
gaagcggtct gataaaacag aatttgcctg gcggcagtag cgcggtggtc ccacctgacc    3240
ccatgccgaa ctcagaagtg aaacgccgta gcgccgatgg tagtgtgggg tctccccatg    3300
cgagagtagg gaactgccag gcatcaaata aaacgaaagg ctcagtcgaa agactgggcc    3360
tttcgtttta tctgttgttt gtcggtgaac gctctcctga gtaggacaaa tccgccggga    3420
gcggatttga acgttgcgaa gcaacggccc ggagggtggc gggcaggacg cccgccataa    3480
actgccaggc atcaaattaa gcagaaggcc atcctgacgg atggccttt tgcgtttcta    3540
caaactcttt tgtttatttt tctaaataca ttcaaatatg tatccgctca tgaccaaaat    3600
cccttaacgt gagttttcgt tccactgagc gtcagacccc gtagaaaaga tcaaaggatc    3660
ttcttgagat cctttttttc tgcgcgtaat ctgctgcttg caaacaaaaa aaccaccgct    3720
accagcggtg gtttgtttgc cggatcaaga gctaccaact ctttttccga ggtaactgg    3780
cttcagcaga gcgcagatac caaatactgt ccttctagtg tagccgtagt taggccacca    3840
cttcaagaac tctgtagcac cgcctacata cctcgctctg ctaatcctgt taccagtggc    3900
tgctgccagt ggcgataagt cgtgtcttac cgggttggac tcaagacgat agttaccgga    3960
taaggcgcag cggtcgggct gaacggggg ttcgtgcaca cagcccagct tggagcgaac    4020
gacctacacc gaactgagat acctacagcg tgagctatga gaaagcgcca cgcttcccga    4080
agggagaaag gcggacaggt atccggtaag cggcagggtc ggaacaggag agcgcacgag    4140
ggagcttcca gggggaaacg cctggtatct ttatagtcct gtcgggtttc gccacctctg    4200
acttgagcgt cgatttttgt gatgctcgtc agggggggcgg agcctatgga aaaacgccag    4260
caacgcggcc ttttttacggt tcctggcctt ttgctggcct tttgctcaca tgttctttcc    4320
tgcgttatcc cctgattctg tggataaccg tattaccgcc tttgagtgag ctgataccgc    4380
tcgccgcagc cgaacgaccg agcgcagcga gtcagtgagc gaggaagcgg aagagcgcct    4440
gatgcggtat tttctcctta cgcatctgtg cggtatttca caccgcatat ggtgcactct    4500
cagtacaatc tgctctgatg ccgcatagtt aagccagtat acactccgct atcgctacgt    4560
gactgggtca tggctgcgcc ccgacacccg ccaacacccg ctgacgcgcc ctgacgggct    4620
tgtctgctcc cggcatccgc ttacagacaa gctgtgaccg tctccgggag ctgcatgtgt    4680
cagaggtttt caccgtcatc accgaaacgc gcgaggcagc agatcaattc gcgcgcgaag    4740
gcgaagcggc atgcataatg tgcctgtcaa atggacgaag cagggattct gcaaacccta    4800
tgctactccg tcaagccgtc aattgtctga ttcgttacca attatgacaa cttgacggct    4860
acatcattca ctttttcttc acaaccggca cggaactcgc tcgggctggc cccggtgcat    4920
ttttaaata cccgcgagaa atagagttga tcgtcaaaac caacattgcg accgacggtg    4980
gcgataggca tccgggtggt gctcaaaagc agcttcgcct ggctgatacg ttggtcctcg    5040
cgccagctta agacgctaat ccctaactgc tggcggaaaa gatgtgacag acgcgacggc    5100
gacaagcaaa catgctgtgc gacgctggcg at                                 5132
```

<210> SEQ ID NO 2
<211> LENGTH: 36
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2

Tyr Thr Ser Leu Ile His Ser Leu Ile Glu Glu Ser Gln Asn Gln Gln

```
                1               5                   10                  15
Glu Lys Asn Glu Gln Glu Leu Leu Gly Leu Asp Lys Trp Ala Ser Leu
                20                  25                  30

Trp Asn Trp Phe
        35
```

<210> SEQ ID NO 3
<211> LENGTH: 472
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
ggcggccaca tccagatccc gccggggctc acggagctgc tgcagggcta cacggtggag      60
gtgctgcgac agcagccgcc tgacctcgtc gaattcgcag tggagtactt cacccgcctg     120
agagaagctc gcgctgagtt ccctaaaccc agcactccac ccggatcttc cggccaccac     180
caccaccacc acggatccta taccagcctg attcatagcc tgattgaaga agccagaac     240 cagcaggaaa aaacgaaca ggaactgctg gaactggata atgggcgag cctgtggaac      300 tggttttgac tcgagcacca ccaccaccac cactgagatc cggctgctaa caaagcccga    360
aaggaagctg agttggctgc tgccaccgct gagcaataac tagcataacc ccttggggcc    420
tctaaacggg tcttgagggg ttttttgctg aaaggaggaa ctatatccgg at            472
```

<210> SEQ ID NO 4
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
                20                  25                  30

Val Glu Tyr Phe Thr Arg Leu Arg Glu Ala Arg Ala
        35                  40
```

<210> SEQ ID NO 5
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

```
Cys Gly His Ile Gln Ile Pro Pro Gly Leu Thr Glu Leu Leu Gln Gly
1               5                   10                  15

Tyr Thr Val Glu Val Leu Arg Gln Gln Pro Pro Asp Leu Val Glu Phe
                20                  25                  30

Ala Val Glu Tyr Phe Thr Arg Leu Arg Glu Ala Arg Ala
            35                  40                  45
```

<210> SEQ ID NO 6
<211> LENGTH: 17
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 6

Gln Ile Glu Tyr Leu Ala Lys Gln Ile Val Asp Asn Ala Ile Gln Gln
1               5                   10                  15

Ala

<210> SEQ ID NO 7
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Cys Gly Gln Ile Glu Tyr Leu Ala Lys Gln Ile Val Asp Asn Ala Ile
1               5                   10                  15

Gln Gln Ala Gly Cys
            20

<210> SEQ ID NO 8
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Ser Leu Arg Glu Cys Glu Leu Tyr Val Gln Lys His Asn Ile Gln Ala
1               5                   10                  15

Leu Leu Lys Asp Ser Ile Val Gln Leu Cys Thr Ala Arg Pro Glu Arg
            20                  25                  30

Pro Met Ala Phe Leu Arg Glu Tyr Phe Glu Arg Leu Glu Lys Glu Glu
        35                  40                  45

Ala Lys
    50

<210> SEQ ID NO 9
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Ser Cys Gly Gly Ser Leu Arg Glu Cys Glu Leu Tyr Val Gln Lys
1               5                   10                  15

His Asn Ile Gln Ala Leu Leu Lys Asp Ser Ile Val Gln Leu Cys Thr
            20                  25                  30

Ala Arg Pro Glu Arg Pro Met Ala Phe Leu Arg Glu Tyr Phe Glu Arg
        35                  40                  45

Leu Glu Lys Glu Glu Ala Lys
    50                  55

<210> SEQ ID NO 10
<211> LENGTH: 23
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 10

Cys Gly Phe Glu Glu Leu Ala Trp Lys Ile Ala Lys Met Ile Trp Ser
1               5                   10                  15

Asp Val Phe Gln Gln Gly Cys
            20

<210> SEQ ID NO 11
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Ser Leu Arg Glu Cys Glu Leu Tyr Val Gln Lys His Asn Ile Gln Ala
1               5                   10                  15

Leu Leu Lys Asp Val Ser Ile Val Gln Leu Cys Thr Ala Arg Pro Glu
            20                  25                  30

Arg Pro Met Ala Phe Leu Arg Glu Tyr Phe Glu Lys Leu Glu Lys Glu
        35                  40                  45

Glu Ala Lys
    50

<210> SEQ ID NO 12
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ser Leu Lys Gly Cys Glu Leu Tyr Val Gln Leu His Gly Ile Gln Gln
1               5                   10                  15

Val Leu Lys Asp Cys Ile Val His Leu Cys Ile Ser Lys Pro Glu Arg
            20                  25                  30

Pro Met Lys Phe Leu Arg Glu His Phe Glu Lys Leu Glu Lys Glu Glu
        35                  40                  45

Asn Arg Gln Ile Leu Ala
    50

<210> SEQ ID NO 13
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ser His Ile Gln Ile Pro Pro Gly Leu Thr Glu Leu Leu Gln Gly Tyr
1               5                   10                  15

Thr Val Glu Val Gly Gln Gln Pro Pro Asp Leu Val Asp Phe Ala Val
            20                  25                  30

Glu Tyr Phe Thr Arg Leu Arg Glu Ala Arg Arg Gln
        35                  40
```

```
<210> SEQ ID NO 14
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ser Ile Glu Ile Pro Ala Gly Leu Thr Glu Leu Leu Gln Gly Phe Thr
1               5                   10                  15

Val Glu Val Leu Arg His Gln Pro Ala Asp Leu Leu Glu Phe Ala Leu
            20                  25                  30

Gln His Phe Thr Arg Leu Gln Gln Glu Asn Glu Arg
        35                  40

<210> SEQ ID NO 15
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15 gagttccta aacccagcac tccacccgga tcttccggc                          39

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

His His His His His His Gly Ser
1               5
```